(12) United States Patent
Powers et al.

(10) Patent No.: US 11,236,049 B2
(45) Date of Patent: Feb. 1, 2022

(54) AMORPHOUS AND CRYSTALLINE FORMS OF IDO INHIBITORS

(71) Applicant: BRISTOL-MYERS SQUIBB COMPANY, Princeton, NJ (US)

(72) Inventors: Jay Patrick Powers, Pacifica, CA (US); Hilary Plake Beck, Emerald Hills, CA (US); Maksim Osipov, Redwood City, CA (US); Maureen Kay Reilly, Burlingame, CA (US); Hunter Paul Shunatona, Oakland, CA (US); James Ross Walker, Verona, WI (US); Mikhail Zibinsky, Redwood City, CA (US); Tamar Rosenbaum, Princeton, NJ (US); Ian Scott Young, Redwood City, CA (US); Jennifer Nelson, Kokomo, IN (US); Petinka Vlahova, West Lafayette, IN (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/624,490

(22) PCT Filed: Jun. 29, 2018

(86) PCT No.: PCT/US2018/040262
§ 371 (c)(1),
(2) Date: Dec. 19, 2019

(87) PCT Pub. No.: WO2019/006283
PCT Pub. Date: Jan. 3, 2019

(65) Prior Publication Data
US 2020/0115342 A1    Apr. 16, 2020

Related U.S. Application Data

(60) Provisional application No. 62/527,855, filed on Jun. 30, 2017.

(51) Int. Cl.
*C07D 215/18*    (2006.01)
*A61K 45/06*    (2006.01)

(52) U.S. Cl.
CPC ............ *C07D 215/18* (2013.01); *A61K 45/06* (2013.01); *C07B 2200/13* (2013.01)

(58) Field of Classification Search
CPC .................. C07D 215/18; C07B 2200/13
See application file for complete search history.

(56) References Cited

U.S. PATENT DOCUMENTS

| 6,627,646 B2 * | 9/2003 | Bakale .................... A61P 37/08 514/322 |
| 2016/0137652 A1 | 5/2016 | Beck et al. |
| 2017/0143649 A1 | 5/2017 | Beck et al. |

FOREIGN PATENT DOCUMENTS

| WO | 2006/029879 | 3/2006 |
| WO | 2006/105021 A2 | 10/2006 |
| WO | 2006/122150 A1 | 11/2006 |
| WO | 2007/005874 A2 | 1/2007 |
| WO | 2007/075598 A2 | 7/2007 |
| WO | 2008/036642 A2 | 3/2008 |
| WO | 2008/036653 A2 | 3/2008 |
| WO | 2008/132601 A1 | 11/2008 |
| WO | 2009/009116 | 1/2009 |
| WO | 2009/044273 | 4/2009 |
| WO | 2009/073620 A2 | 6/2009 |
| WO | 2010/019570 | 2/2010 |
| WO | 2010/077634 A1 | 7/2010 |
| WO | 2011/028683 | 3/2011 |
| WO | 2011/056652 | 5/2011 |
| WO | 2011/070024 | 6/2011 |
| WO | 2011/107553 A1 | 9/2011 |
| WO | 2011/109400 A2 | 9/2011 |
| WO | 2011/131407 A1 | 10/2011 |
| WO | 2011/140249 A2 | 11/2011 |
| WO | 2012/032433 | 3/2012 |
| WO | 2012/142237 A1 | 10/2012 |
| WO | 2012/145493 A1 | 10/2012 |
| WO | 2013/079174 | 6/2013 |
| WO | 2013/087699 | 6/2013 |
| WO | 2013/119716 A1 | 8/2013 |
| WO | 2013/132044 A1 | 9/2013 |
| WO | 2013/169264 A1 | 11/2013 |
| WO | 2014/008218 | 1/2014 |
| WO | 2014/036357 A1 | 3/2014 |
| WO | 2016/073770 A1 | 5/2016 |
| WO | 2019/006292 A1 | 1/2019 |

OTHER PUBLICATIONS

CMU Pharmaceutical polymorphism, internet p. 1-3 printout Apr. 3, 2008. (Year: 2002).*
Singhal et al., "Drug Polymorphism, etc.," Advanced Drug Delivery reviews 56, p. 335-347. (Year: 2004).*
Concise Encyclopedia Chemistry, NY: Walter de Gruyter, 872-873. (Year: 1993).*
Jain et al., Polymorphism in Pharmacy, Indian Drugs, 23(6) 315-329. (Year: 1979).*
Muzaffar et al,, "Polymorphism and Drug, etc.," J of Pharm. (Lahore), 1(1), 59-66. (Year: 1979).*
U.S. Pharmacopia #23, National Formulary #18, 1843-1844. (Year: 1995).*

(Continued)

*Primary Examiner* — Patricia L Morris

(74) *Attorney, Agent, or Firm* — BakerHostetler

(57) ABSTRACT

The present disclosure relates to amorphous and crystalline forms of (R)-N-(4-chlorophenyl)-2-((1S,4S)-4-(6-fluoroquinolin-4-yl) cyclohexyl)propanamide and its salts and hydrates, processes for their production, pharmaceutical compositions comprising them, and methods of treatment using them.

4 Claims, 29 Drawing Sheets

(56) References Cited

OTHER PUBLICATIONS

Doelker, english translation of S.T.P. Pratiques, 9(5), 399-409, pp. 1-33. (Year: 1999).*

Doelker, english translation of Ann. Pharm. Fr., 60: 161-176, pp. 1-39. (Year: 2002).*

Taday et al, "Using Terahertz, etc.," J of Pharm. Sci., 92(4), 831-838. (Year: 2003).*

Otuska et al., "Effect of Polymorphic, etc.," Chem. Pharm. Bull., 47(6) 852-856. (Year: 1999).*

Barich et al, 3-Methylglutaric acid as a 13C solid-state NMR standard, Solid state nuclear magnetic resonance, Oct. 1, 2006;30(3-4):125-129.

Bennett et al, Heteronuclear decoupling in rotating solids, The Journal of chemical physics, Oct. 22, 1995;103(16):6951-6958.

Goldstein et al, J. Biological efficacy of a chimeric antibody to the epidermal growth factor receptor in a human tumor xenograft model, Clin. Cancer Res, 1995;1:1311-1318.

Kohl et al, Inhibition of farnesyltransferase induces regression of mammary and salivary carcinomas in ras transgenic mice, Nature medicine, Aug. 1995;1(8):792-797.

Metz G et al, Ramped-amplitude cross polarization in magic-angle-spinning NMR, Journal of Magnetic Resonance, Series A, Oct. 1, 1994;110(2):219-227.

Sausville, Cyclin-dependent kinase modulators studied at the NCI: pre-clinical and clinical studies, Current Medicinal Chemistry—Anti-Cancer Agents, Jan. 1, 2003;3(1):47-56.

Scheller et al, Paclitaxel balloon coating, a novel method for prevention and therapy of restenosis, Circulation, Aug. 17, 2004;110(7):810-814.

Sekulic, A direct linkage between the phosphoinositide 3-kinase-AKT signaling pathway and the mammalian target of rapamycin in mitogen-stimulated and transformed cells, Cancer research, Jul. 1, 2000;60(13):3504-3513.

Vlahos et al, A specific inhibitor of phosphatidylinositol 3-kinase, 2-(4-morpholinyl)-8-phenyl-4H-1-benzopyran-4-one (LY294002), Journal of Biological Chemistry, Feb. 18, 1994;269(7):5241-5248.

Byrn et al., Pharmaceutical Solids: A Strategic Approach to Regulatory Considerations, Pharmaceutical Research, Jan. 1, 1995, vol. 12, No. 7, pp. 945-954.

EPC Communication dated Oct. 23, 2020 for EP18823337.3 / 3644993, dated Oct. 23, 2020.

Mino R. Caira, Ed., Crystalline Polymorphism of Organic Compounds, Jan. 1, 1998, Topics in Current Chemistry, vol. 198, pp. 163-208.

Serajuddin, Abu T.M., Salt Formation to Improve Drug Solubility, Aug. 24, 2007, Advanced Drug Delivery Reviews, Science Direct, 59, pp. 603-616.

\* cited by examiner

X-ray diffractogram of Compound 1 free base monohydrate, Form 2 ssNMR of Compound 1 free base hydrate Form 2

FTIR of Compound 1 Free Base Hydrate Form 2

Compound 1 free base monohydrate Form 2 DSC

Compound 1 free base monohydrate Form 2 TGA

FT-Raman Compound 1 Free Base Monohydrate Form 2

X-ray diffractogram of Compound 1 free base, Form 4 ssNMR Compound 1 free base Form 4

DSC Compound 1 free base Form 4

TGA Compound 1 free base Form 4

X-ray diffractogram of amorphous Compound 1 free base

SsNMR of Compound 1 free base amorphous

FT-IR of Compound 1 free base amorphous

FT-Raman Compound 1 Free base amorphous

X-ray diffractogram of Compound 1 methanesulfonic acid salt, Form 1 ssNMR of Compound 1 MSA Salt Form 1

FTIR Compound 1 MSA Salt Form 1

Compound 1 MSA Salt Form 1 DSC

FT-Raman Compound 1 MSA Form 1

Compound 1 MSA Salt Form 1 TGA

X-ray diffractogram of amorphous Compound 1 methanesulfonic acid.

ssNMR Compound 1 MSA Salt Amorphous

FT-Raman Compound 1 MSA salt amorphous

XRPD of Compound 1 MSA salt monohydrate Form 2

Compound 1 MSA salt hydrate Form 2 DSC

Compound 1 MSA Salt hydrate Form 2 TGA

Micro-dissolution profiles of Compound 1 MSA Salt Form 1, Compound 1 HCl (Amorphous), and Crystalline Compound 1 HCl in FaSSIF and FeSSIF at Simulated 150 mg Human Dose.

Micro-dissolution profiles of Compound 1 MSA Salt Form 1, Compound 1 Free Base (Amorphous), and Compound 1 Free Base Form 2 in FaSSIF and FeSSIF at 0.2 mg/mL, n=3-4.

AMORPHOUS AND CRYSTALLINE FORMS OF IDO INHIBITORS

CROSS-REFERENCE TO RELATED APPLICATIONS

This application is the National Stage Application of International Patent Application No. PCT/US2018/040262, filed Jun. 29, 2018, which claims the benefit of U.S. Provisional Application No. 62/527,855, filed Jun. 30, 2017, the entirety of which is incorporated by reference herein.

TECHNICAL FIELD

The present disclosure relates to solid forms of (R)-N-(4-chlorophenyl)-2-((1S,4S)-4-(6-fluoroquinolin-4-yl)cyclohexyl)propanamide and its salts and hydrates, processes for their production, pharmaceutical compositions comprising them, and methods of treatment using them.

BACKGROUND (R)-N-(4-chlorophenyl)-2-((1S,4S)-4-(6-fluoroquinolin-4-yl)cyclohexyl)propanamide, also referred to herein as Compound 1, has the below structure:

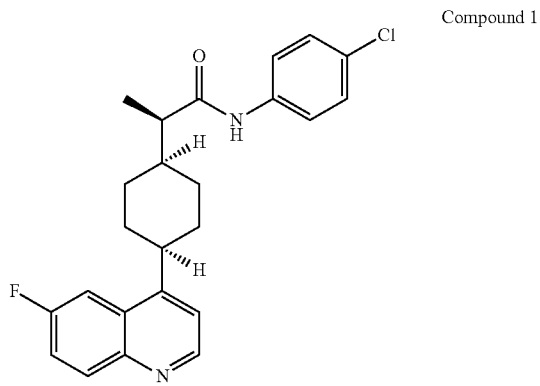 [SMILES: C[C@@H](C(=O)Nc1ccc(Cl)cc1)[C@H]1CC[C@@H](c2ccnc3ccc(F)cc32)CC1]

Compound 1

Compound 1 is a potent inhibitor of indoleamine 2,3-dioxygenase (IDO; also known as IDO1), which is an IFN-γ target gene that plays a role in immunomodulation. Compound 1 is being investigated as a treatment for cancer and other diseases. Compound 1 has been previously described in WO2016/073770.

A compound, as a free base, hydrate, solvate, or salt, can exist in amorphous form and/or one or more crystalline forms, each having different physical properties, for example, different X-ray diffraction patterns (XRPD or PXRD) and different thermal behavior. The free base, hydrate, solvate, and salt forms of a compound can also differ with respect to their individual stabilities, processing, formulation, dissolution profile, bioavailability, and the like.

New forms of (R)-N-(4-chlorophenyl)-2-((1S,4S)-4-(6-fluoroquinolin-4-yl)cyclohexyl)propanamide, having desirable and beneficial chemical and physical properties are needed. There is also a need for reliable and reproducible methods for the manufacture, purification, and formulation of Compound 1 (and its hydrates, solvates, salt, and hydrated salt forms) to facilitate commercialization. The present disclosure is directed to these, as well as other important aspects.

SUMMARY

The present disclosure is directed to solid forms of (R)-N-(4-chlorophenyl)-2-((1S,4S)-4-(6-fluoroquinolin-4-yl)cyclohexyl)propanamide (Compound 1) including solid forms of (R)-N-(4-chlorophenyl)-2-((1S,4S)-4-(6-fluoroquinolin-4-yl)cyclohexyl)propanamide free base, solid forms of (R)-N-(4-chlorophenyl)-2-((1S,4S)-4-(6-fluoroquinolin-4-yl)cyclohexyl)propanamide monohydrate, solid forms of (R)-N-(4-chlorophenyl)-2-((1S,4S)-4-(6-fluoroquinolin-4-yl)cyclohexyl)propanamide methanesulfonic acid salt, and solid forms of (R)-N-(4-chlorophenyl)-2-((1S,4S)-4-(6-fluoroquinolin-4-yl)cyclohexyl)propanamide methanesulfonic acid salt monohydrate. Compositions comprising the described solid forms, as well as methods of preparing and using them in therapy, are also described.

DETAILED DESCRIPTION OF ILLUSTRATIVE EMBODIMENTS

Figure 1:
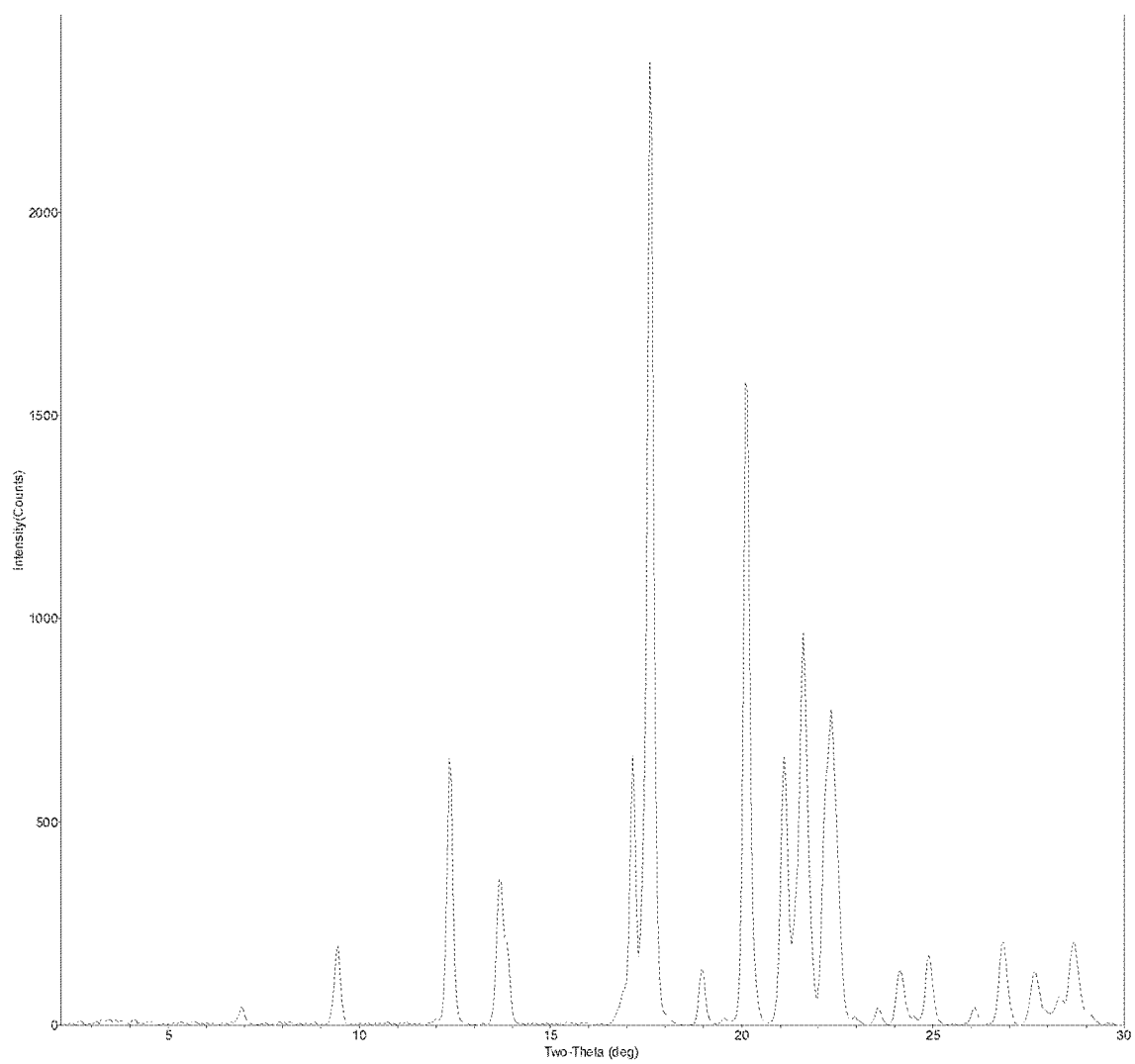
FIG. 1 depicts a powder X-ray diffractogram of Compound 1 free base monohydrate, Form 2.

The present disclosure is directed to solid forms of Compound 1, for example, Compound 1 (free base), Compound 1 monohydrate (free base), and Compound 1 methanesulfonic acid (MSA) salt, Compound 1 MSA salt monohydrate, as well as the production of such solid forms, pharmaceutical compositions comprising such solid forms, and methods of treating diseases mediated by IDO using such solid forms. Designations of the disclosed solid forms should not be construed as limiting with respect to any other substance possessing similar or identical physical and chemical characteristics, but rather, it should be understood that these designations are identifiers that should be interpreted according to the characterization information disclosed herein.

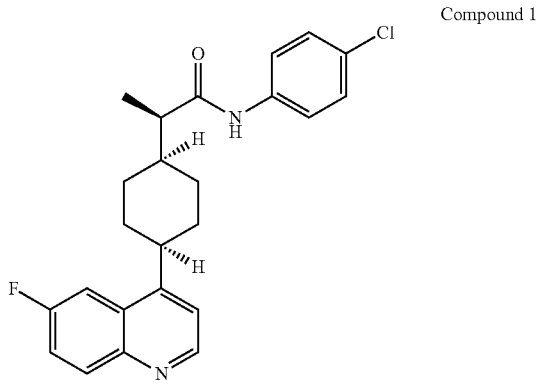 [SMILES: C[C@@H](C(=O)Nc1ccc(Cl)cc1)[C@H]1CC[C@@H](c2ccnc3ccc(F)cc32)CC1]

Compound 1

Compound 1 Free Base Hydrate

In one embodiment, the disclosure is directed a solid form of Compound 1 (free base) that is a monohydrate. For example, the solid form of Compound 1 free base monohydrate comprises about 1 molecule of water per molecule of Compound 1 free base.

In a preferred aspects, the solid form of Compound 1 (free base) hydrate is a crystalline form of Compound 1 (free base) monohydrate, referred to herein as Compound 1 free base monohydrate Form 2. Compound 1 free base monohydrate Form 2 has a desirable stability profile.

Compound 1 free base monohydrate Form 2 can be characterized by an X-ray diffraction pattern having one peak, or at least one peak, selected from 9.4, 12.4, 17.2, 17.6, 20.1, 21.1, and 21.6 degrees 2θ±0.2 degrees 2θ. Compound 1 free base monohydrate Form 2 can also be characterized by an X-ray diffraction pattern having two peaks selected from 9.4, 12.4, 17.2, 17.6, 20.1, 21.1, and 21.6 degrees 2θ±0.2 degrees 2θ. Compound 1 free base monohydrate Form 2 can also be characterized by an X-ray diffraction pattern having three peaks selected from 9.4, 12.4, 17.2, 17.6, 20.1, 21.1, and 21.6 degrees 2θ±0.2 degrees 2θ. Compound 1 free base monohydrate Form 2 can also be characterized by an X-ray diffraction pattern having four peaks selected from 9.4, 12.4, 17.2, 17.6, 20.1, 21.1, and 21.6 degrees 2θ±0.2 degrees 2θ. Compound 1 free base monohydrate Form 2 can also be characterized by an X-ray diffraction pattern having five peaks selected from 9.4, 12.4, 17.2, 17.6, 20.1, 21.1, and 21.6 degrees 2θ±0.2 degrees 2θ. Compound 1 free base monohydrate Form 2 can also be characterized by an X-ray diffraction pattern having six peaks selected from 9.4, 12.4, 17.2, 17.6, 20.1, 21.1, and 21.6 degrees 2θ±0.2 degrees 2θ. Compound 1 free base monohydrate Form 2 can also be characterized by an X-ray diffraction pattern having peaks at 9.4, 12.4, 17.2, 17.6, 20.1, 21.1, and 21.6 degrees 2θ±0.2 degrees 2θ.

Diffraction peak positions for Compound 1 free base monohydrate Form 2, at room temperature, based on a high quality pattern collected with a diffractometer (CuKα) with a spinning capillary with 2θ calibrated with a NIST, or other suitable standard, are shown in Table 1 and Table 1A.

TABLE 1

| Characteristic diffraction peak positions for Compound 1 free base monohydrate Form 2 degrees 2θ ± 0.2 |
|---|
| 9.4 |
| 12.4 |
| 17.2 |
| 17.6 |
| 20.1 |
| 21.1 |
| 21.6 |

TABLE 1A

| Peak Listing for Compound 1 free base monohydrate Form 2 degrees 2θ ± 0.2 |
|---|
| 6.9 |
| 9.4 |
| 12.4 |
| 13.7 |
| 13.9 |
| 17.2 |
| 17.6 |
| 19.0 |
| 20.1 |
| 21.1 |
| 21.6 |
| 22.3 |
| 23.6 |
| 24.2 |
| 24.9 |
| 26.1 |
| 26.8 |
| 27.7 |
| 28.3 |
| 28.7 |

Compound 1 free base monohydrate Form 2 can be characterized by an X ray diffraction pattern having at least one peak selected from the peaks listed in Table 1A.

Compound 1 free base monohydrate Form 2 can also be characterized by an X-ray diffraction pattern substantially as depicted in FIG. 1.

Table 2 sets forth the single crystal X-ray data for Compound 1 Free Base monohydrate, Form 2.

TABLE 2

Single Crystal X-Ray Data for
Compound 1 Free Base Monohydrate, Form 2

| | |
|---|---|
| Temperature | room temperature |
| Wavelength | 1.54178 Å |
| Crystal system, space group | Monoclinic, C2 |
| Unit cell dimensions | a = 25.404(1) Å    alpha = 90° |
| | b = 10.0423(6) Å    beta = 91.851(3)° |
| | c = 8.8156(5) Å    gamma = 90° |
| Volume | 2247.8(2) Å$^3$ |
| Calculated density | 1.267 g/cm$^3$ |
| Formula units per unit cell | 4 |

Table 3 sets forth the atomic coordinates for Compound 1 Free Base monohydrate, Form 2.

TABLE 3

Atomic Coordinates of Compound 1 Free Base hydrate, Form 2

| Atom | X | Y | Z |
|---|---|---|---|
| Cl1 | 0.9315(1) | 0.7764(2) | −0.4727(1) |
| F1 | 0.4666(1) | 0.3834(3) | 0.2165(4) |
| N1 | 0.7695(1) | 0.8741(3) | −0.0183(3) |
| N2 | 0.4216(1) | 0.9155(3) | 0.2075(3) |
| O1 | 0.8056(1) | 0.7905(3) | 0.2000(3) |
| C1 | 0.8090(1) | 0.8444(3) | −0.1225(3) |
| C2 | 0.8601(1) | 0.8075(4) | −0.0778(4) |
| C3 | 0.8974(1) | 0.7881(5) | −0.1872(4) |
| C4 | 0.8841(1) | 0.8006(4) | −0.3377(4) |
| C5 | 0.8337(2) | 0.8338(4) | −0.3835(4) |
| C6 | 0.7963(1) | 0.8565(3) | −0.2758(4) |
| C7 | 0.7699(1) | 0.8502(3) | 0.1316(3) |
| C8 | 0.7248(1) | 0.9096(3) | 0.2179(4) |
| C9 | 0.7015(1) | 0.8014(4) | 0.3205(4) |
| C10 | 0.5836(1) | 0.7989(4) | 0.3160(3) |
| C11 | 0.6690(1) | 0.7014(4) | 0.2284(5) |
| C12 | 0.6145(1) | 0.7526(3) | 0.1786(4) |
| C13 | 0.6687(1) | 0.8556(5) | 0.4498(4) |
| C14 | 0.6155(1) | 0.9081(4) | 0.3965(3) |
| C15 | 0.5276(1) | 0.8384(3) | 0.2725(3) |
| C16 | 0.4875(1) | 0.7398(3) | 0.2481(3) |
| C17 | 0.4351(1) | 0.7839(4) | 0.2203(3) |
| C18 | 0.4595(2) | 1.0022(4) | 0.2239(5) |
| C19 | 0.5123(1) | 0.9688(4) | 0.2591(5) |
| C20 | 0.4974(2) | 0.6011(4) | 0.2490(4) |
| C21 | 0.3940(1) | 0.6887(4) | 0.2044(4) |
| C22 | 0.4047(2) | 0.5560(4) | 0.2082(4) |
| C23 | 0.4566(2) | 0.5159(4) | 0.2253(4) |
| C24 | 0.7470(2) | 1.0312(4) | 0.3017(6) |
| O1W | 0.8172(1) | 0.5088(3) | 0.1604(4) |
| H1 | 0.7416 | 0.9123 | −0.0557 |
| H2 | 0.8691 | 0.7960 | 0.0244 |
| H3 | 0.9319 | 0.7664 | −0.1577 |
| H5 | 0.8247 | 0.8411 | −0.4862 |
| H6 | 0.7622 | 0.8801 | −0.3067 |
| H8 | 0.6974 | 0.9391 | 0.1446 |
| H9 | 0.7312 | 0.7526 | 0.3674 |
| H10 | 0.5817 | 0.7234 | 0.3860 |
| H11A | 0.6648 | 0.6214 | 0.2884 |
| H11B | 0.6881 | 0.6774 | 0.1388 |
| H12A | 0.5951 | 0.6822 | 0.1260 |
| H12B | 0.6182 | 0.8263 | 0.1086 |
| H13A | 0.6637 | 0.7852 | 0.5232 |
| H13B | 0.6882 | 0.9267 | 0.5007 |
| H14A | 0.6202 | 0.9822 | 0.3276 |
| H14B | 0.5965 | 0.9403 | 0.4829 |
| H18 | 0.4511 | 1.0918 | 0.2116 |
| H19 | 0.5371 | 1.0361 | 0.2734 |
| H20 | 0.5314 | 0.5689 | 0.2656 |

TABLE 3-continued

Atomic Coordinates of Compound 1 Free Base hydrate, Form 2

| Atom | X | Y | Z |
|---|---|---|---|
| H21 | 0.3594 | 0.7174 | 0.1913 |
| H22 | 0.3777 | 0.4937 | 0.1995 |
| H24A | 0.7618 | 1.0915 | 0.2303 |
| H24B | 0.7738 | 1.0035 | 0.3741 |
| H24C | 0.7192 | 1.0750 | 0.3536 |
| H1W | 0.846(3) | 0.485(7) | 0.174(6) |
| H2W | 0.817(3) | 0.598(8) | 0.159(7) |

Figure 1A:
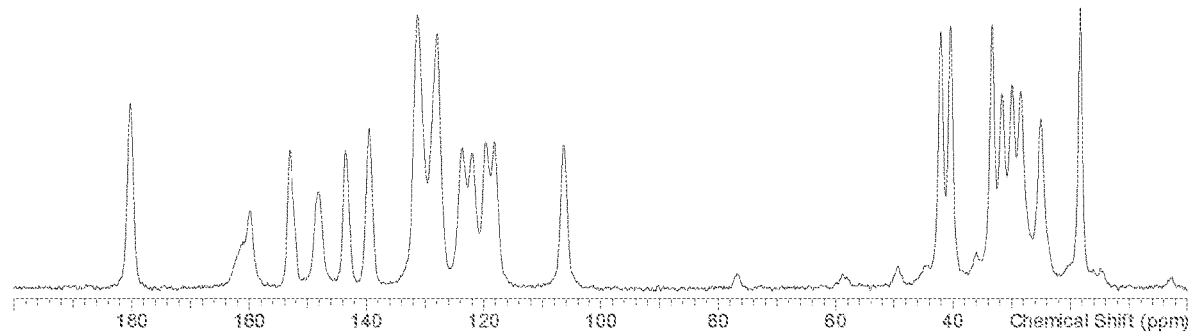
FIG. 1A depicts a ssNMR spectrum of Compound 1 free base monohydrate Form 2.

An ssNMR spectrum of Compound 1 free base monohydrate is depicted in FIG. 1A. ssNMR of Compound 1 free base hydrate Form 2 produces the following peaks:

| ppm (±0.2) |
|---|
| 180.4 |
| 160.0 |
| 153.1 |
| 148.2 |
| 143.6 |
| 139.5 |
| 131.3 |
| 127.9 |
| 123.7 |
| 122.1 |
| 119.7 |
| 118.3 |
| 106.5 |
| 42.0 |
| 40.4 |
| 33.3 |
| 31.6 |
| 29.9 |
| 28.4 |
| 25.0 |
| 18.3 |

Figure 1B:
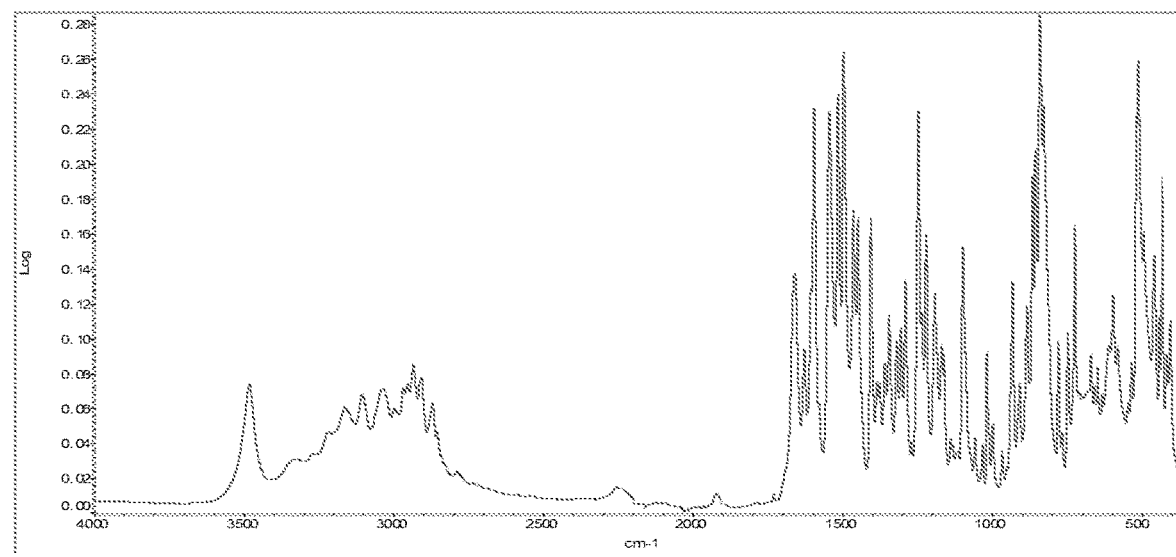
FIG. 1B depicts an FT-IR of Compound 1 Free Base monohydrate Form 2.

An FT-IR spectrum of Compound 1 free base monohydrate Form 2 is depicted in FIG. 1B. The FTIR of Compound 1 free base monohydrate produces at least the following peaks:

| cm$^{-1}$ (±1) |
|---|
| 3481 |
| 3104 |
| 2933 |
| 2867 |
| 1660 |
| 1595 |
| 1542 |
| 1544 |
| 1495 |
| 1405 |
| 1244 |
| 1097 |
| 931 |

Figure 1C:
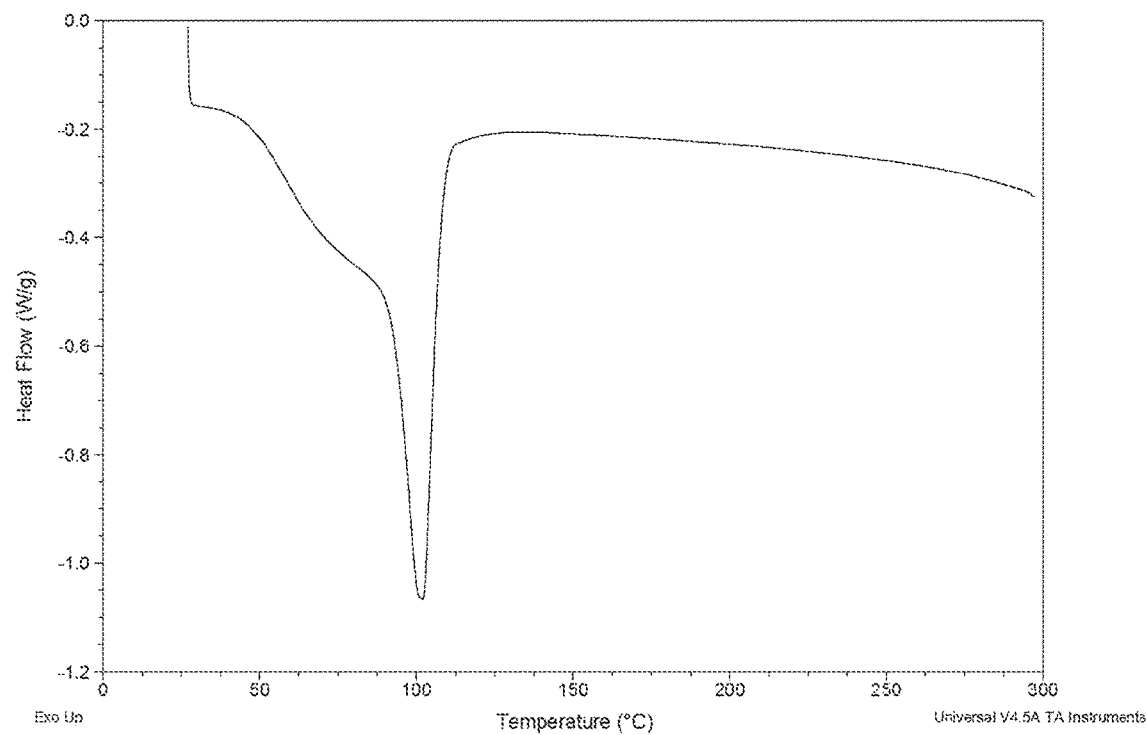
FIG. 1C depicts a Differential Scanning Calorimetry (DSC) thermogram of Compound 1 free base monohydrate Form 2.

A DSC thermogram of Compound 1 free base monohydrate Form 2 is depicted in FIG. 1C.

Figure 1D:
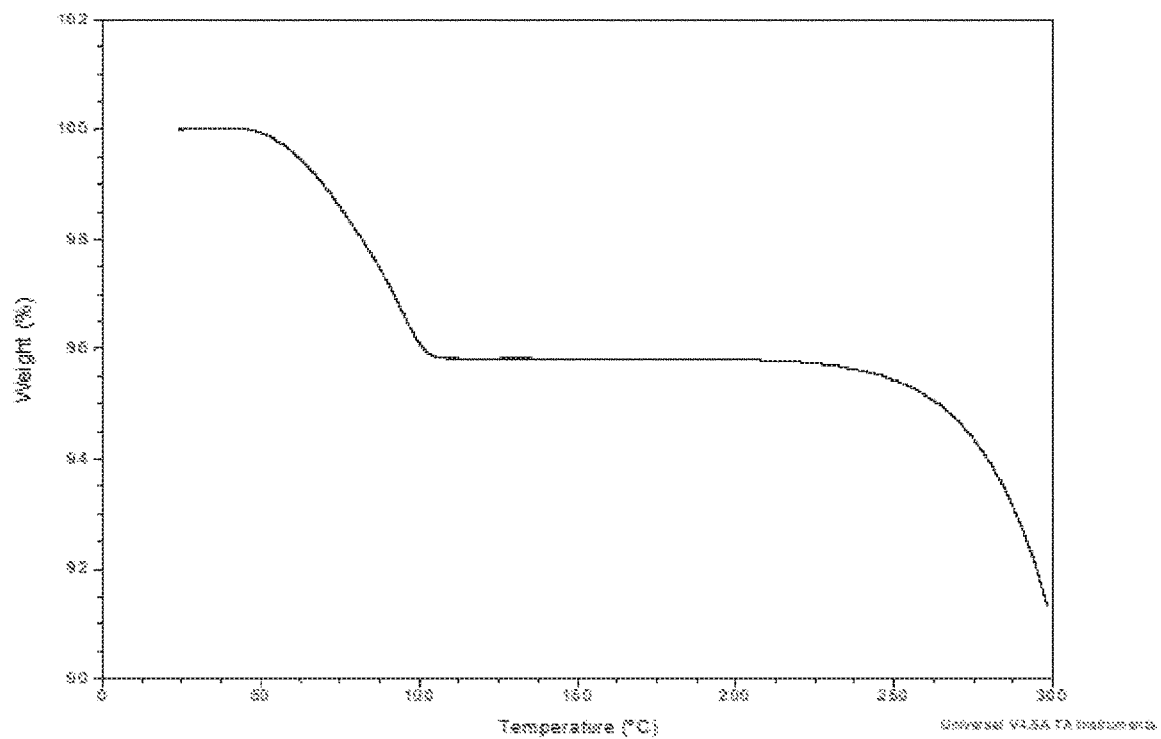
FIG. 1D depicts a Thermogravimetric Analysis (TGA) thermogram of Compound 1 free base monohydrate Form 2.

A TGA thermogram of Compound 1 freebase monohydrate Form 2 is depicted in FIG. 1D.

Figure 1E:
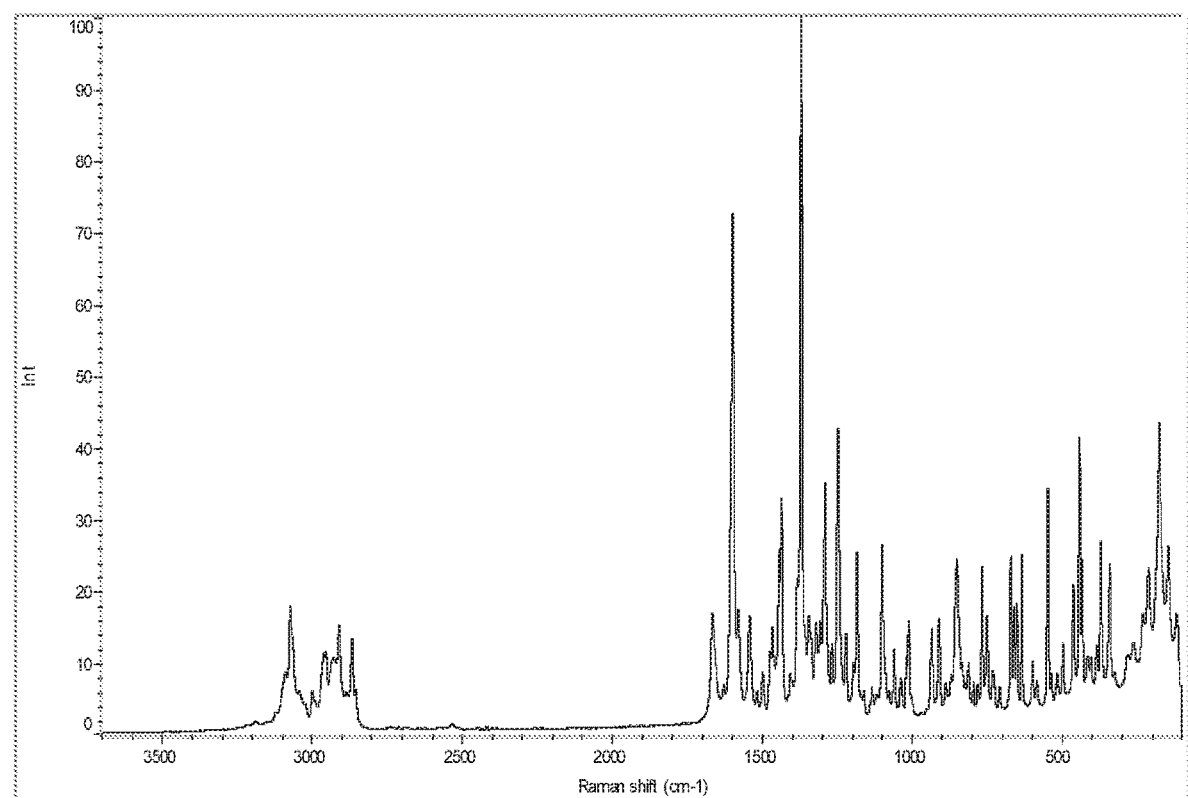
FIG. 1E depicts an FT-Raman spectrum of Compound 1 free base monohydrate Form 2.

An FT-Raman spectrum of Compound 1 free base monohydrate Form 2 is depicted in FIG. 1E. The FT-Raman of Compound 1 free base monohydrate produces at least the following peaks:

| cm$^{-1}$ (±1) |
| --- |
| 141 |
| 172 |
| 208 |
| 337 |
| 366 |
| 430 |
| 439 |
| 458 |
| 544 |
| 629 |
| 668 |
| 762 |
| 847 |
| 1096 |
| 1180 |
| 1244 |
| 1287 |
| 1368 |
| 1379 |
| 1433 |
| 1440 |
| 1594 |

Compound 1 free base monohydrate Form 2 can be in substantially pure form, that is, having a purity of about 90% or greater, based on the weight of the compound, as determined by HPLC (High Performance Liquid Chromatography). For example, Compound 1 free base monohydrate Form 2 can have a purity of about 90, 91, 92, 93, 94, 95, 96, 97, 98, 99, or 100%. The remaining material can comprise other solid forms of Compound 1 and/or reaction impurities and/or processing impurities arising from its preparation.

Mixtures of Compound 1 free base monohydrate Form 2 with other solid forms of Compound 1 are also within the scope of the disclosure. In these embodiments, such mixtures can comprise less than 90%, based on the weight of the mixture, of Compound 1 free base monohydrate Form 2. For example, mixtures can comprise 85, 80, 75, 70, 65, 60, 55, 50, 45, 40, 35, 30, 25, 20, 15, 10, or about 5%, by weight of the mixture, of Compound 1 free base monohydrate Form 2.

Compound 1 Free Base

In one embodiment, the disclosure is directed to a crystalline form of Compound 1 (free base), referred to herein as Form 4. Compound 1 free base Form 4 has desirable handleability and stability properties that are sufficient to enable the manufacture of solid dosage forms on commercial scale.

Compound 1 free base Form 4 can be characterized by an X ray diffraction pattern having one peak, or at least one peak, selected from 7.6, 12.0, 13.5, 14.4, 17.6, 20.1, 20.7, and 22.0 degrees 2θ±0.2 degrees 2θ. Compound 1 free base Form 4 can also be characterized by an X ray diffraction pattern having two peaks selected from 7.6, 12.0, 13.5, 14.4, 17.6, 20.1, 20.7, and 22.0 degrees 2θ±0.2 degrees 2θ. Compound 1 free base Form 4 can also be characterized by an X ray diffraction pattern having three peaks selected from 7.6, 12.0, 13.5, 14.4, 17.6, 20.1, 20.7, and 22.0 degrees 2θ±0.2 degrees 2θ. Compound 1 free base Form 4 can also be characterized by an X ray diffraction pattern having four peaks selected from 7.6, 12.0, 13.5, 14.4, 17.6, 20.1, 20.7, and 22.0 degrees 2θ±0.2 degrees 2θ. Compound 1 free base Form 4 can also be characterized by an X ray diffraction pattern having five peaks selected from 7.6, 12.0, 13.5, 14.4, 17.6, 20.1, 20.7, and 22.0 degrees 2θ±0.2 degrees 2θ. Compound 1 free base Form 4 can also be characterized by an X ray diffraction pattern having six peaks selected from 7.6, 12.0, 13.5, 14.4, 17.6, 20.1, 20.7, and 22.0 degrees 2θ±0.2 degrees 2θ. Compound 1 free base Form 4 can also be characterized by an X ray diffraction pattern having seven peaks selected from 7.6, 12.0, 13.5, 14.4, 17.6, 20.1, 20.7, and 22.0 degrees 2θ±0.2 degrees 2θ. Compound 1 free base Form 4 can also be characterized by an X ray diffraction pattern having peaks at 7.6, 12.0, 13.5, 14.4, 17.6, 20.1, 20.7, and 22.0 degrees 2θ±0.2 degrees 2θ.

Diffraction peak positions for Compound 1 free base Form 4, at room temperature, based on a high quality pattern collected with a diffractometer (CuKα) with a spinning capillary with 2θ calibrated with a NIST, or other suitable standard, are shown in Table 4 and Table 4A.

TABLE 4

Characteristic diffraction peak positions for Compound 1
free base Form 4
degrees
2θ ± 0.2

| |
| --- |
| 7.6 |
| 12.0 |
| 13.5 |
| 14.4 |
| 17.6 |
| 20.1 |
| 20.7 |
| 22.0 |

TABLE 4A

Peak Listing for Compound 1 free base Form 4
degrees
2θ ± 0.2

| |
| --- |
| 7.6 |
| 10.3 |
| 10.5 |
| 11.4 |
| 12.0 |
| 13.5 |
| 14.4 |
| 15.2 |
| 16.3 |
| 17.4 |
| 17.6 |
| 18.9 |
| 19.1 |
| 20.1 |
| 20.7 |
| 21.1 |
| 21.5 |
| 22.0 |
| 22.6 |
| 23.0 |
| 26.1 |
| 27.0 |
| 27.4 |
| 27.7 |
| 28.8 |

Compound 1 free base Form 4 can be characterized by an X ray diffraction pattern having at least one peak selected from the peaks listed in Table 4A.

Figure 2:
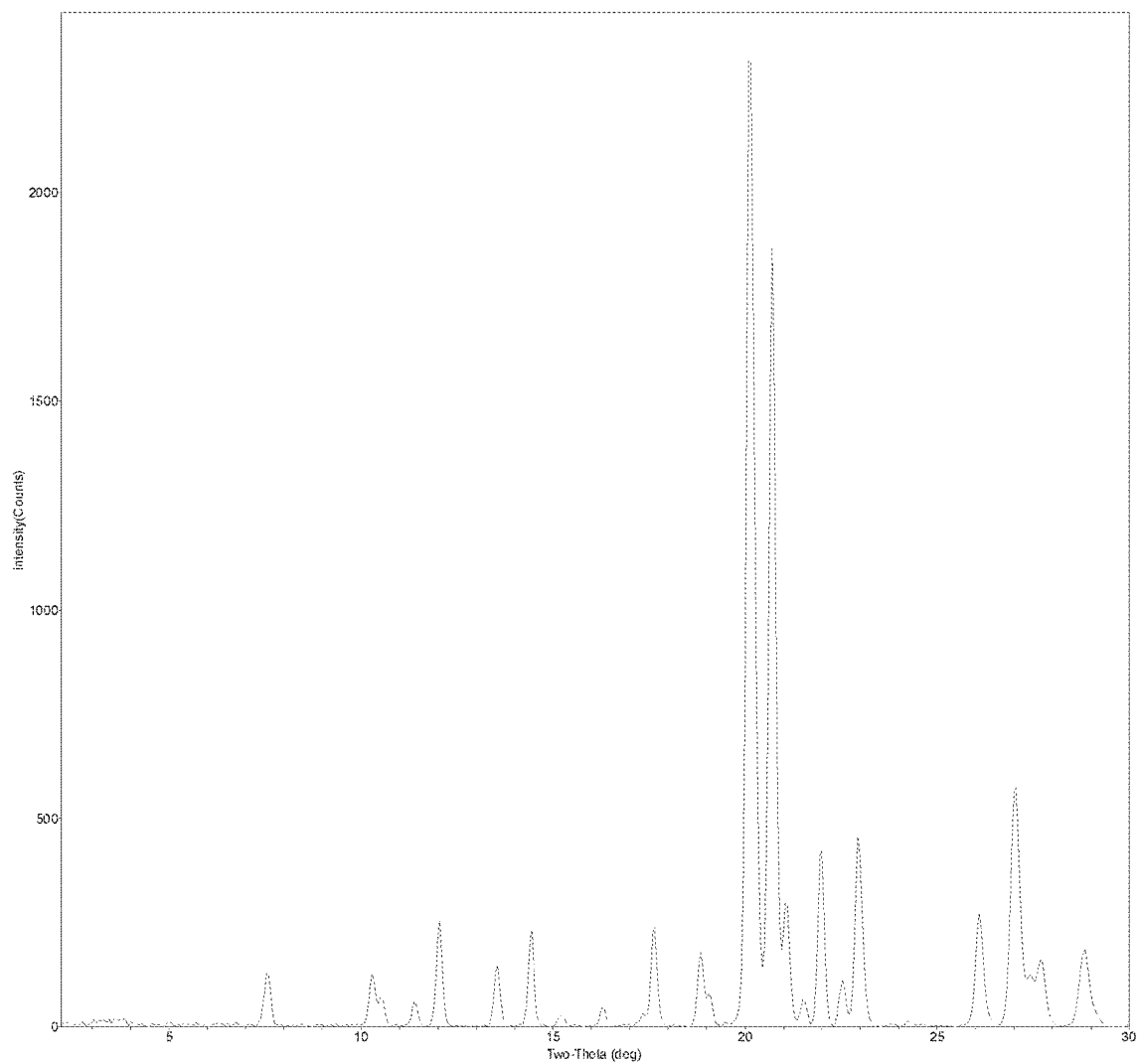
FIG. 2 depicts a powder X-ray diffractogram of Compound 1 free base, Form 4.

Compound 1 free base Form 4 can also be characterized by an X-ray diffraction pattern substantially as depicted in FIG. 2.

Table 5 sets forth the single crystal X-ray data for Compound 1 Free Base, Form 4.

TABLE 5

Single Crystal X-Ray Data for Compound 1 Free Base, Form 4

| | |
|---|---|
| Temperature | room temperature |
| Wavelength | 1.54178 Å |
| Crystal system, space group | Monoclinic, P2$_1$ |
| Unit cell dimensions | a = 8.648(1) Å, alpha = 90 |
| | b = 5.1322(8) Å, beta = 97.105(8)° |
| | c = 23.367(3) Å, gamma = 90 |
| Volume | 029.1(3) Å$^3$ |
| Calculated density | 1.326 g/cm$^3$ |
| Formula units per unit cell | 2 |

Table 6 sets forth the atomic coordinates for Compound 1 Free Base, Form 4.

TABLE 6

Atomic Coordinates of Compound 1 Free Base, Form 4

| Atom | X | Y | Z |
|---|---|---|---|
| Cl1 | 0.8004(2) | 0.2652(4) | 0.3629(1) |
| F1 | 1.1246(3) | 0.2782(6) | 1.0468(1) |
| N1 | 0.7171(4) | 0.1912(6) | 0.6093(1) |
| N2 | 1.3913(4) | −0.2846(7) | 0.8863(1) |
| O1 | 0.6832(4) | 0.6147(5) | 0.6310(1) |
| C1 | 0.6913(4) | 0.3024(7) | 0.7082(1) |
| C2 | 0.6971(4) | 0.3875(7) | 0.6464(1) |
| C3 | 1.0494(4) | 0.3737(7) | 0.7598(1) |
| C4 | 1.0496(4) | 0.3071(7) | 0.8235(1) |
| C5 | 0.8839(4) | 0.2214(7) | 0.8332(1) |
| C6 | 0.7634(4) | 0.4316(8) | 0.8142(1) |
| C7 | 0.7625(4) | 0.5106(7) | 0.7505(1) |
| C8 | 0.9293(4) | 0.5839(7) | 0.7407(1) |
| C9 | 1.1730(4) | 0.1091(7) | 0.8455(1) |
| C10 | 1.2521(4) | −0.0343(8) | 0.8098(2) |
| C11 | 1.3606(4) | −0.225(1) | 0.8317(2) |
| C12 | 1.3155(4) | −0.1434(7) | 0.9241(2) |
| C13 | 1.3477(4) | −0.2058(9) | 0.9829(2) |
| C14 | 1.2089(4) | 0.0605(7) | 0.9063(1) |
| C15 | 1.1460(4) | 0.2041(8) | 0.9493(1) |
| C16 | 1.1854(5) | 0.1387(8) | 1.0055(2) |
| C17 | 1.2845(5) | −0.0653(9) | 1.0234(2) |
| C18 | 0.7706(5) | 0.243(1) | 0.4346(2) |
| C19 | 0.8427(5) | 0.0488(9) | 0.4681(2) |
| C20 | 0.8239(5) | 0.0343(9) | 0.5259(2) |
| C21 | 0.7315(4) | 0.2123(7) | 0.5498(1) |
| C22 | 0.6556(4) | 0.4029(8) | 0.5156(2) |
| C23 | 0.6753(5) | 0.4174(9) | 0.4575(2) |
| C24 | 0.5211(5) | 0.240(1) | 0.7147(2) |
| H1 | 0.7215 | 0.0364 | 0.6234 |
| H1A | 0.7526 | 0.1423 | 0.7150 |
| H3A | 1.1521 | 0.4342 | 0.7533 |
| H3B | 1.0261 | 0.2182 | 0.7367 |
| H4 | 1.0728 | 0.4680 | 0.8455 |
| H5A | 0.8570 | 0.0628 | 0.8117 |
| H5B | 0.8818 | 0.1838 | 0.8738 |
| H6A | 0.7850 | 0.5844 | 0.8384 |
| H6B | 0.6607 | 0.3682 | 0.8199 |
| H7 | 0.6984 | 0.6678 | 0.7441 |
| H8A | 0.9313 | 0.6185 | 0.6999 |
| H8B | 0.9586 | 0.7432 | 0.7616 |
| H10 | 1.2343 | −0.0059 | 0.7703 |
| H11 | 1.4139 | −0.3145 | 0.8056 |
| H13 | 1.4131 | −0.3452 | 0.9942 |
| H15 | 1.0783 | 0.3420 | 0.9392 |
| H17 | 1.3073 | −0.1052 | 1.0623 |
| H19 | 0.9042 | −0.0731 | 0.4520 |
| H20 | 0.8739 | −0.0965 | 0.5487 |
| H22 | 0.5913 | 0.5216 | 0.5312 |
| H23 | 0.6237 | 0.5453 | 0.4343 |
| H24A | 0.4588 | 0.3933 | 0.7070 |
| H24B | 0.5139 | 0.1805 | 0.7532 |
| H24C | 0.4841 | 0.1055 | 0.6877 |

Figure 2A:
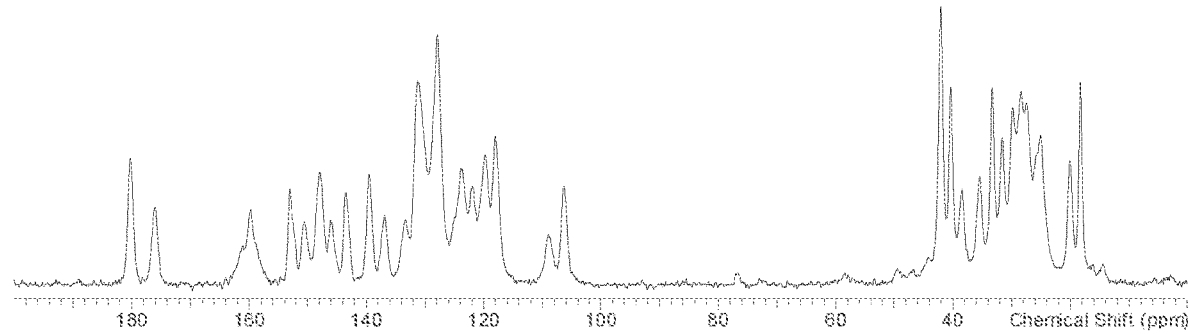
FIG. 2A depicts an ssNMR spectrum of Compound 1 free base Form 4.

A ssNMR spectrum is depicted in FIG. 2A. Compound 1 free base Form 4 produces the following ssNMR peaks:

| ppm (±0.2) |
|---|
| 180.3 |
| 176.2 |
| 159.1 |
| 153.1 |
| 147.9 |
| 143.6 |
| 139.6 |
| 137.0 |
| 131.2 |
| 127.9 |
| 123.8 |
| 119.8 |
| 118.1 |
| 109.0 |
| 106.4 |
| 42.1 |
| 40.4 |
| 38.4 |
| 35.4 |
| 33.3 |
| 31.6 |
| 29.9 |
| 28.4 |
| 25.1 |
| 20.1 |
| 18.3 |

Figure 2B:
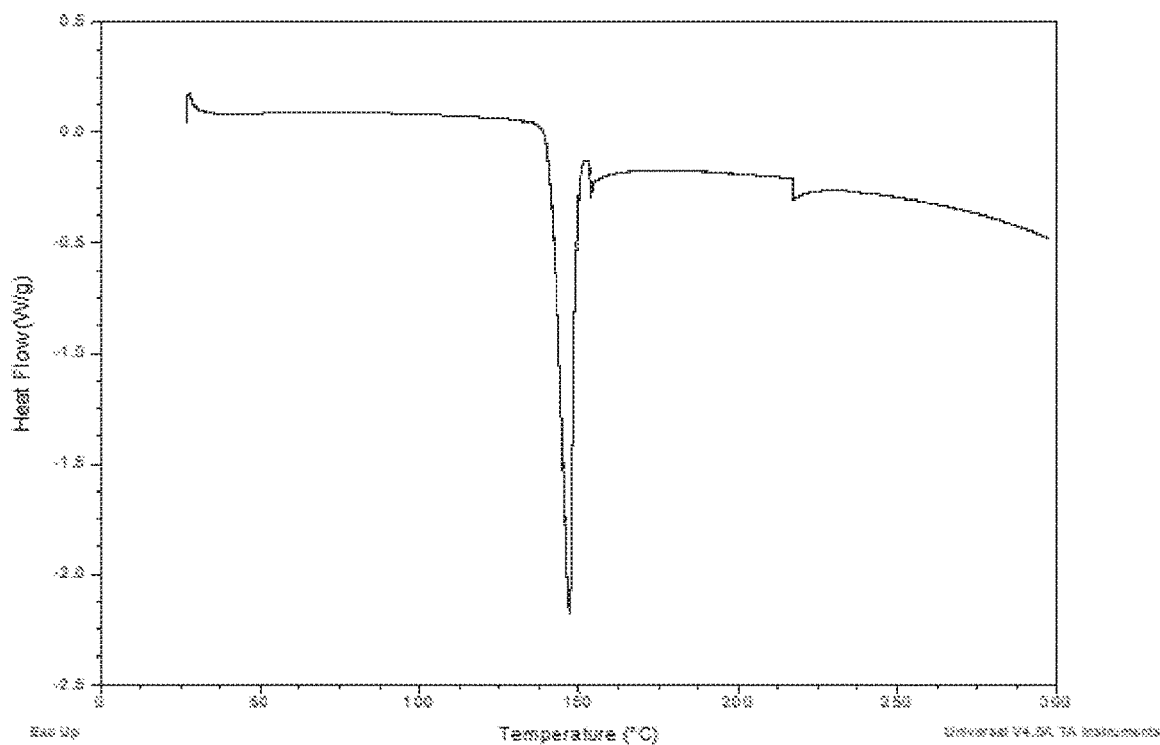
FIG. 2B depicts a DSC thermogram of Compound 1 free base Form 4.

A DSC thermogram a Compound 1 free base Form 4 is depicted in FIG. 2B.

Figure 2C:
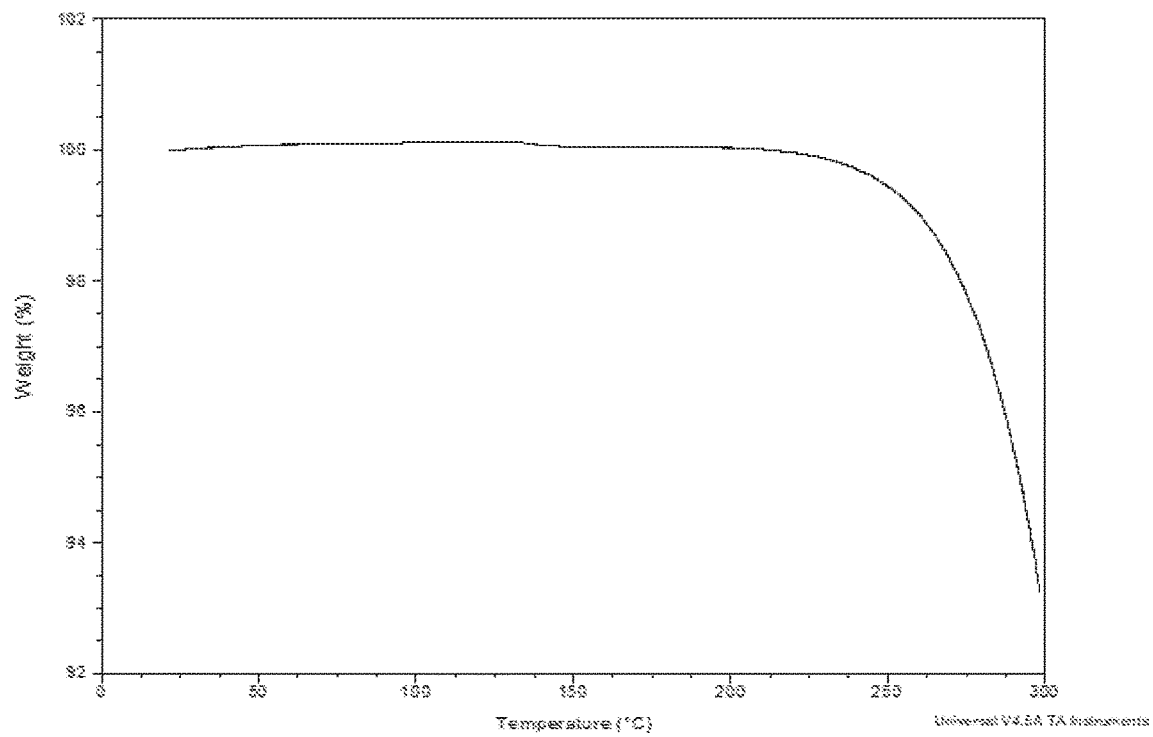
FIG. 2C depicts a TGA thermogram of Compound 1 Free base Form 4.

A TGA thermogram of Compound 1 free base Form 4 is depicted in FIG. 2C.

Figure 3:
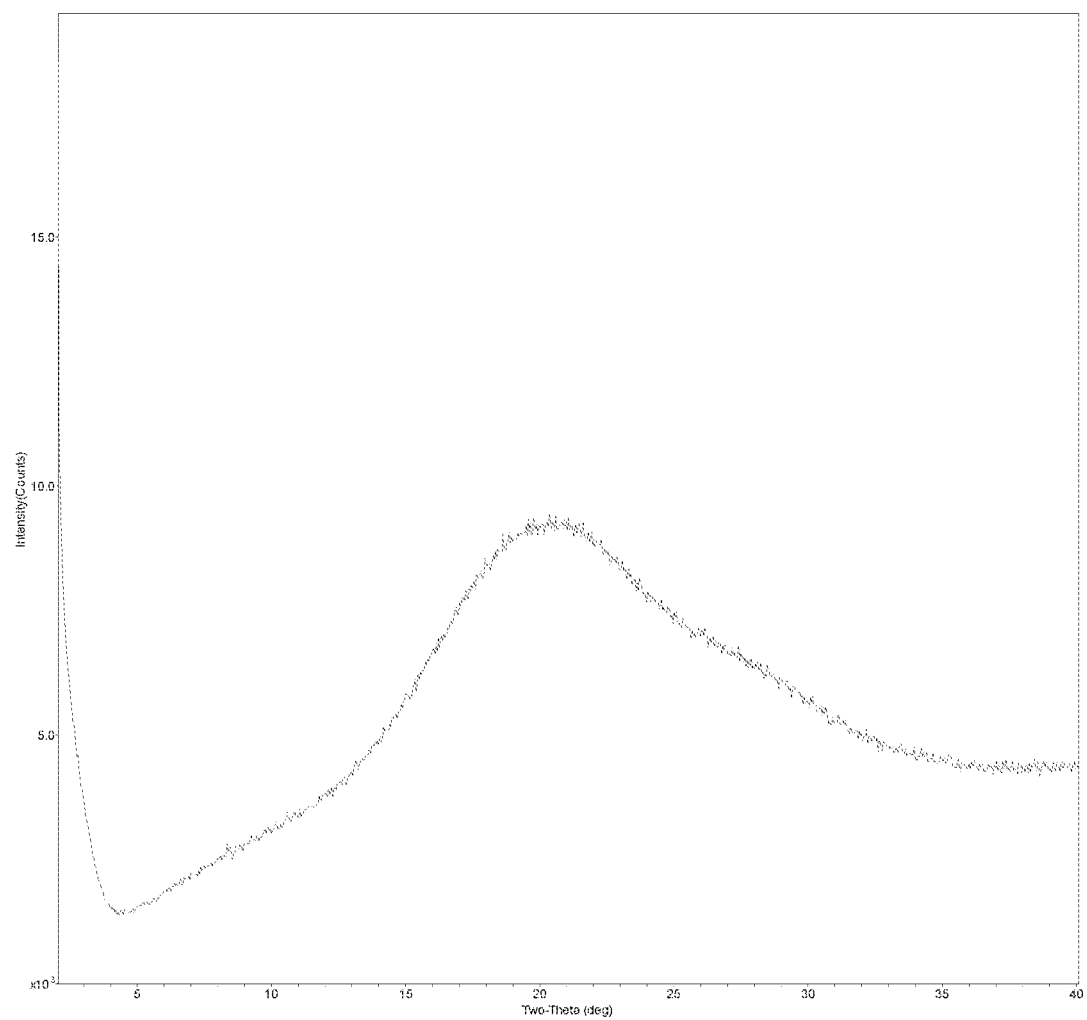
FIG. 3 depicts a powder X-ray diffractogram of amorphous Compound 1 free base.
Figure 3A:
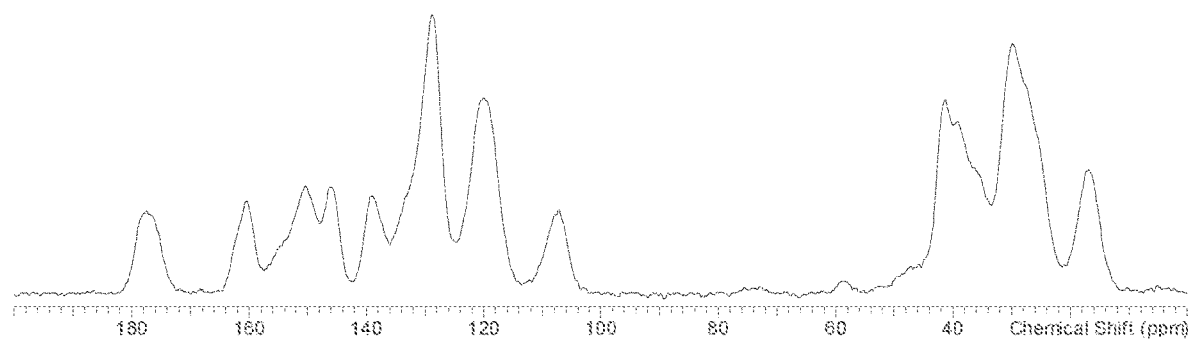
FIG. 3A depicts a ssNMR spectrum of Compound 1 free base amorphous.

Amorphous Compound 1 free base is also within the scope of this disclosure. A PXRD of amorphous Compound 1 free base is depicted in FIG. 3. A solid-state NMR of Compound 1 free base amorphous is depicted in FIG. 3A. The ssNMR of Compound 1 free base amorphous produces the following peaks:

| ppm (±0.2) |
|---|
| 177.4 |
| 160.6 |
| 150.6 |
| 146.0 |
| 139.2 |
| 128.9 |
| 120.1 |
| 107.3 |
| 41.2 |
| 29.9 |
| 17.1 |

Figure 3B:
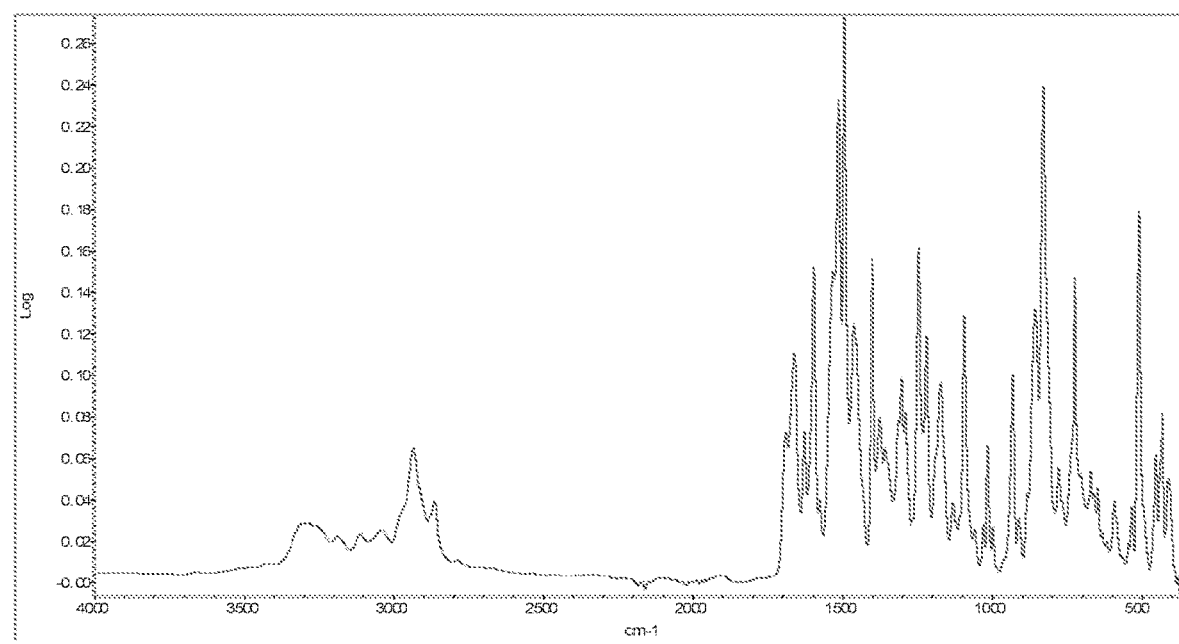
FIG. 3B depicts a FT-IR spectrum of Compound 1 free base amorphous.

A FT-IR spectrum of Compound 1 free base amorphous is depicted in FIG. 3B. The FT-IR spectrum of Compound 1 free base amorphous produces the following peaks:

| cm$^{-1}$ (±1) |
|---|
| 2933 |
| 2862 |
| 1689 |
| 1660 |
| 1596 |
| 1514 |
| 1492 |
| 1400 |
| 1244 |
| 1091 |

Figure 3C:
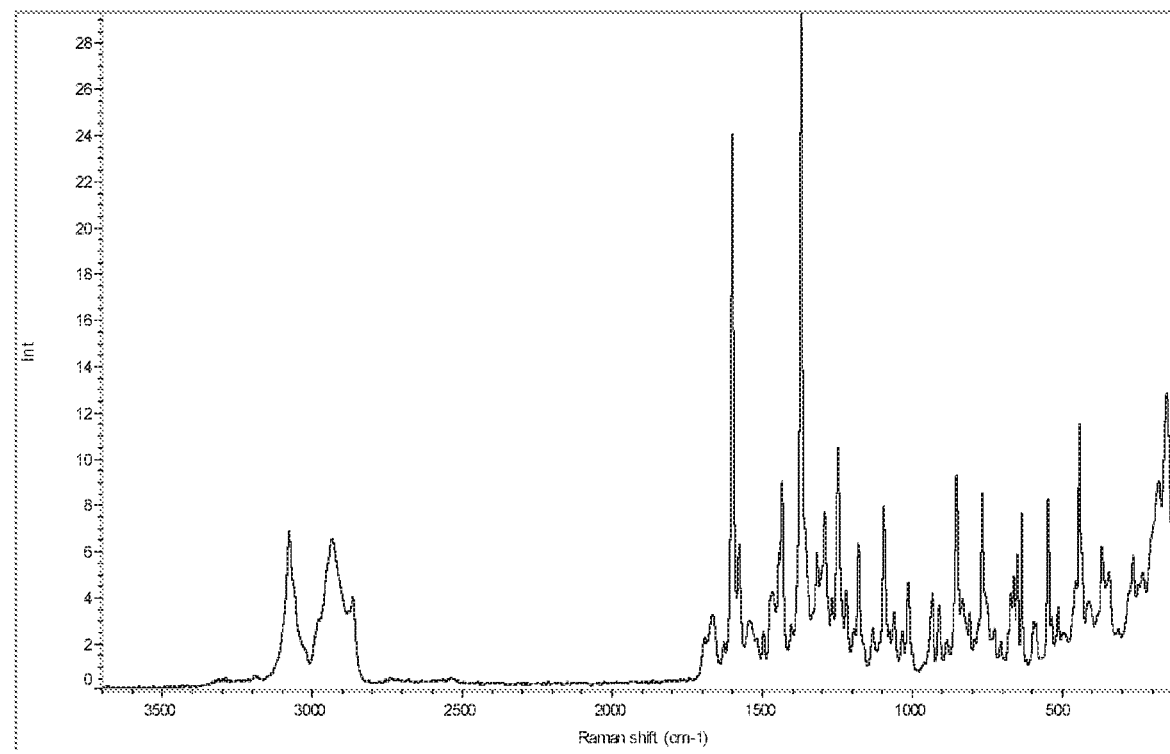
FIG. 3C depicts a FT-Raman spectrum of Compound 1 free base amorphous.

A FT-Raman spectrum of Compound 1 free base amorphous is depicted in FIG. 3C. The FT-Raman spectrum of Compound 1 free base amorphous produces the following peaks:

| cm$^{-1}$ (±1) |
| --- |
| 147 |
| 173 |
| 362 |
| 439 |
| 543 |
| 629 |
| 762 |
| 848 |
| 1090 |
| 1174 |
| 1244 |
| 1288 |
| 1367 |
| 1430 |
| 1573 |
| 1595 |
| 2931 |
| 3074 |

Compound 1 free base Form 4 can be in substantially pure form, that is, having a purity of about 90% or greater, based on the weight of the compound, as determined by HPLC. For example, Compound 1 free base Form 4 can have a purity of about 90, 91, 92, 93, 94, 95, 96, 97, 98, 99, or 100%. The remaining material can comprise other solid forms of Compound 1 and/or reaction impurities and/or processing impurities arising from its preparation.

Mixtures of Compound 1 free base Form 4 with other solid forms of Compound 1 are also within the scope of the disclosure. In these embodiments, such mixtures can comprise less than 90%, based on the weight of the mixture, of Compound 1 free base Form 4. For example, mixtures can comprise 85, 80, 75, 70, 65, 60, 55, 50, 45, 40, 35, 30, 25, 20, 15, 10, or about 5%, by weight of the mixture, of Compound 1 free base Form 4.

Amorphous Compound 1 free base can be in substantially pure form, that is, having a purity of about 90% or greater, based on the weight of the compound, as determined by HPLC. For example, amorphous Compound 1 free base can have a purity of about 90, 91, 92, 93, 94, 95, 96, 97, 98, 99, or 100%. The remaining material can comprise other solid forms of Compound 1 and/or reaction impurities and/or processing impurities arising from its preparation.

Mixtures of Amorphous Compound 1 free base with other solid forms of Compound 1 are also within the scope of the disclosure. In these embodiments, such mixtures can comprise less than 90%, based on the weight of the mixture, of Amorphous Compound 1 free base. For example, mixtures can comprise 85, 80, 75, 70, 65, 60, 55, 50, 45, 40, 35, 30, 25, 20, 15, 10, or about 5%, by weight of the mixture, of Amorphous Compound 1 free base.

Compound 1 MSA Salt

In one embodiment, the disclosure is directed to crystalline forms of Compound 1 methanesulfonic acid (MSA) salt. In some aspects, the crystalline form of the Compound 1 MSA salt is non-solvated. In other aspects, the crystalline form of the Compound 1 MSA salt is non-hydrated (i.e., anhydrous). In yet other aspects, the crystalline form of the Compound 1 MSA salt is non-solvated and non-hydrated (i.e., anhydrous).

In preferred aspects of the disclosure, the Compound 1 MSA salt is a Compound 1 mono-MSA salt. In particularly preferred aspects, the crystalline form of Compound 1 mono-MSA salt is referred to herein as Form 1. Compound 1 mono-MSA salt, in particular Compound 1 mono-MSA salt Form 1 has increased oral bioavailability when administered as a solid dosage form, as compared to Compound 1 free base.

Compound 1 MSA salt Form 1 can be characterized by an X-ray diffraction pattern having one peak, or at least one peak, selected from 12.2, 12.6, 13.4, 14.8, 16.4, 16.8, 19.6, and 24.0 degrees 2θ±0.2 degrees 2θ. Compound 1 MSA salt Form 1 can also be characterized by an X-ray diffraction pattern having two peaks selected from 12.2, 12.6, 13.4, 14.8, 16.4, 16.8, 19.6, and 24.0 degrees 2θ±0.2 degrees 2θ. Compound 1 MSA salt Form 1 can also be characterized by an X-ray diffraction pattern having three peaks selected from 12.2, 12.6, 13.4, 14.8, 16.4, 16.8, 19.6, and 24.0 degrees 2θ±0.2 degrees 2θ. Compound 1 MSA salt Form 1 can also be characterized by an X-ray diffraction pattern having four peaks selected from 12.2, 12.6, 13.4, 14.8, 16.4, 16.8, 19.6, and 24.0 degrees 2θ±0.2 degrees 2θ. Compound 1 MSA salt Form 1 can also be characterized by an X-ray diffraction pattern having five peaks selected from 12.2, 12.6, 13.4, 14.8, 16.4, 16.8, 19.6, and 24.0 degrees 2θ±0.2 degrees 2θ. Compound 1 MSA salt Form 1 can also be characterized by an X-ray diffraction pattern having six peaks selected from 12.2, 12.6, 13.4, 14.8, 16.4, 16.8, 19.6, and 24.0 degrees 2θ±0.2 degrees 2θ. Compound 1 MSA salt Form 1 can also be characterized by an X-ray diffraction pattern having seven peaks selected from 12.2, 12.6, 13.4, 14.8, 16.4, 16.8, 19.6, and 24.0 degrees 2θ±0.2 degrees 2θ. Compound 1 MSA salt Form 1 can also be characterized by an X-ray diffraction pattern having peaks at 12.2, 12.6, 13.4, 14.8, 16.4, 16.8, 19.6, and 24.0 degrees 2θ±0.2 degrees 2θ.

Diffraction peak positions for Compound 1 MSA salt Form 1, at room temperature, based on a high quality pattern collected with a diffractometer (CuKα) with a spinning capillary with 2θ calibrated with a NIST, or other suitable standard, are shown in Table 7 and Table 7A.

TABLE 7

| Characteristic diffraction peak positions for Compound 1 MSA Salt Form 1 |
| --- |
| degrees 2θ ± 0.2 |
| 12.2 |
| 12.6 |
| 13.4 |
| 14.8 |
| 16.4 |
| 16.8 |
| 19.6 |
| 24.0 |

TABLE 7A

| Peak Listing for Compound 1 MSA Salt Form 1 |
| --- |
| degrees 2θ ± 0.2 |
| 8.1 |
| 9.9 |
| 10.5 |
| 11.7 |
| 12.2 |
| 12.6 |
| 13.4 |
| 14.8 |
| 16.0 |

TABLE 7A-continued

Peak Listing for Compound 1 MSA Salt Form 1
degrees
2θ ± 0.2

16.4
16.8
17.8
18.4
18.7
19.6
19.8
20.2
20.8
21.4
21.8
21.9
22.7
23.3
23.6
24.0
24.7
25.4
26.1
26.4
27.2
27.6
27.8
28.4

Compound 1 MSA salt Form 1 can be characterized by an X ray diffraction pattern at least one peak selected from the peaks listed in Table 7A.

Figure 4:
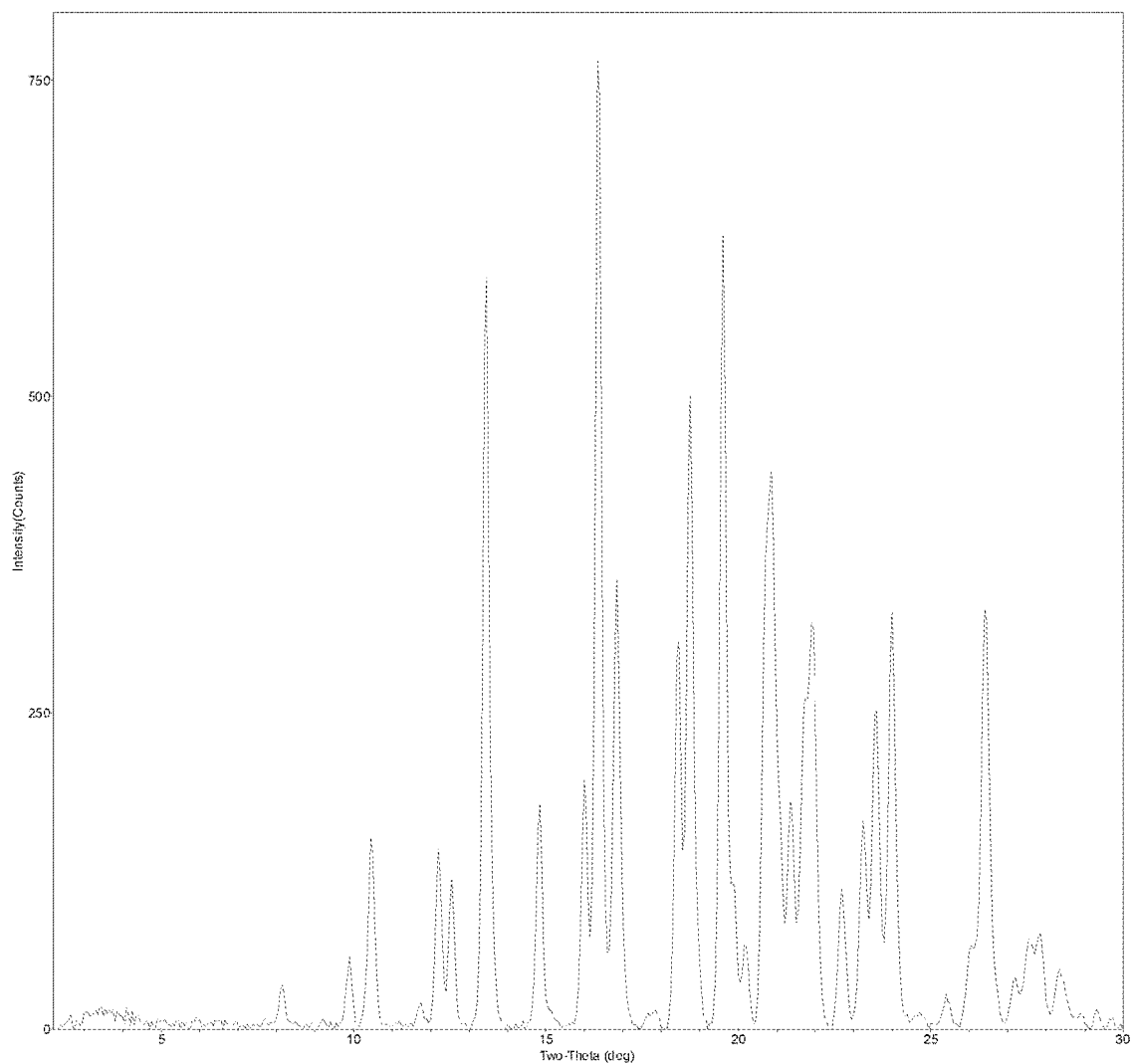
FIG. 4 depicts a powder X-ray diffractogram of Compound 1 mono-methanesulfonic acid salt (MSA salt), Form 1.

Compound 1 MSA salt Form 1 can also be characterized by an X-ray diffraction pattern substantially as depicted in FIG. 4.

Table 8 sets forth the single crystal X-ray data for Compound 1 MSA salt, Form 1.

TABLE 8

Single crystal X-ray data for Compound 1 MSA salt, Form 1

| | |
|---|---|
| Temperature | room temperature |
| Wavelength | 1.54178 Å |
| Crystal system, space group | Orthorhombic, $P2_12_12_1$ |
| Unit cell dimensions | a = 10.4855(2) Å    alpha = 90 |
| | b = 14.1015(3) Å    beta = 90 |
| | c = 16.9033(4) Å    gamma = 90° |
| Volume | 2499.34(9) Å$^3$ |
| Calculated density | 1.347 g/cm$^3$ |
| Formula units per unit cell | 4 |

Table 9 sets forth atomic coordinate of Compound 1 MSA salt, Form 1

TABLE 9

Atomic Coordinates of Compound 1 MSA Salt, Form 1

| Atom | X | Y | Z |
|---|---|---|---|
| Cl1 | 0.6693(1) | 0.6888(1) | 0.0394(1) |
| F1 | 0.6567(3) | 0.9364(2) | 0.7979(2) |
| N1 | 0.3065(3) | 0.7782(2) | 0.2968(2) |
| N2 | 0.3061(4) | 0.6553(2) | 0.7924(2) |
| O1 | 0.2978(6) | 0.9365(2) | 0.2854(2) |
| C1 | 0.5541(4) | 0.7114(2) | 0.1116(2) |
| C2 | 0.5277(4) | 0.6452(2) | 0.1691(2) |
| C3 | 0.4422(4) | 0.6679(2) | 0.2283(2) |
| C4 | 0.3844(3) | 0.7563(2) | 0.2316(2) |
| C5 | 0.4097(4) | 0.8209(3) | 0.1715(2) |
| C6 | 0.4935(4) | 0.7983(3) | 0.1115(2) |
| C7 | 0.2683(5) | 0.8647(2) | 0.3206(2) |
| C8 | 0.1851(4) | 0.8680(2) | 0.3942(2) |
| C9 | 0.0484(5) | 0.8872(4) | 0.3676(4) |

TABLE 9-continued

Atomic Coordinates of Compound 1 MSA Salt, Form 1

| Atom | X | Y | Z |
|---|---|---|---|
| C10 | 0.2364(3) | 0.9441(2) | 0.4503(2) |
| C11 | 0.3691(3) | 0.9189(3) | 0.4815(2) |
| C12 | 0.3663(3) | 0.8414(3) | 0.5450(2) |
| C13 | 0.2757(3) | 0.8687(2) | 0.6127(2) |
| C14 | 0.1436(3) | 0.8876(3) | 0.5803(2) |
| C15 | 0.1489(4) | 0.9669(3) | 0.5192(2) |
| C16 | 0.2826(4) | 0.7953(2) | 0.6779(2) |
| C17 | 0.3809(4) | 0.7999(2) | 0.7367(2) |
| C18 | 0.3907(4) | 0.7275(2) | 0.7945(2) |
| C19 | 0.2134(5) | 0.6503(3) | 0.7400(3) |
| C20 | 0.2003(4) | 0.7200(3) | 0.6808(2) |
| C21 | 0.4745(4) | 0.8715(3) | 0.7395(2) |
| C22 | 0.5667(4) | 0.8681(3) | 0.7955(2) |
| C23 | 0.5741(5) | 0.7981(3) | 0.8530(2) |
| C24 | 0.4881(5) | 0.7276(3) | 0.8521(2) |
| C1S | 0.2647(6) | 0.4955(4) | 1.0224(3) |
| S1S | 0.2704(1) | 0.4633(1) | 0.9229(1) |
| O1S | 0.3834(3) | 0.510(1) | 0.8927(2) |
| O2S | 0.1583(3) | 0.5000(2) | 0.8844(2) |
| O3S | 0.2810(4) | 0.3638(2) | 0.9191(2) |
| H1 | 0.2803 | 0.7310 | 0.3245 |
| H2 | 0.5669 | 0.5861 | 0.1681 |
| H3 | 0.4229 | 0.6230 | 0.2668 |
| H5 | 0.3697 | 0.8798 | 0.1718 |
| H6 | 0.5092 | 0.8415 | 0.0711 |
| H8 | 0.1885 | 0.8062 | 0.4207 |
| H9A | 0.0403 | 0.9524 | 0.3520 |
| H9B | −0.0091 | 0.8743 | 0.4105 |
| H9C | 0.0279 | 0.8470 | 0.3235 |
| H10 | 0.2454 | 1.0024 | 0.4193 |
| H11A | 0.4082 | 0.9754 | 0.5034 |
| H11B | 0.4217 | 0.8976 | 0.4377 |
| H12A | 0.4516 | 0.8321 | 0.5659 |
| H12B | 0.3384 | 0.7822 | 0.5216 |
| H13 | 0.3070 | 0.9285 | 0.6349 |
| H14A | 0.0869 | 0.9055 | 0.6231 |
| H14B | 0.1103 | 0.8304 | 0.5560 |
| H15A | 0.0636 | 0.9785 | 0.4993 |
| H15B | 0.1784 | 1.0245 | 0.5447 |
| H19 | 0.1559 | 0.6002 | 0.7422 |
| H20 | 0.1355 | 0.7148 | 0.6435 |
| H21 | 0.4730 | 0.9209 | 0.7031 |
| H23 | 0.6375 | 0.8000 | 0.8914 |
| H24 | 0.4927 | 0.6791 | 0.8893 |
| H1S1 | 0.1887 | 0.4703 | 1.0460 |
| H1S2 | 0.2642 | 0.5634 | 1.0267 |
| H1S3 | 0.3381 | 0.4706 | 1.0492 |
| H2N | 0.317(4) | 0.602(3) | 0.831(2) |

Figure 4A:
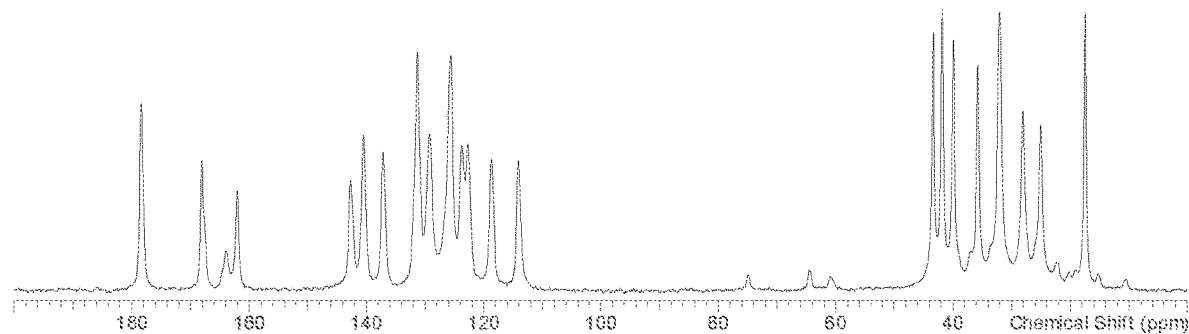
FIG. 4A depicts a ssNMR spectrum of Compound 1 MSA salt Form 1.

A ssNMR of Compound 1 MSA salt Form 1 is depicted in FIG. 4A. The ssNMR of Compound 1 MSA salt Form 1 produces the following peaks:

| ppm (±0.2) |
|---|
| 178.4 |
| 168.2 |
| 162.1 |
| 142.7 |
| 140.5 |
| 137.3 |
| 131.3 |
| 129.3 |
| 125.7 |
| 123.7 |
| 122.8 |
| 118.7 |
| 114.1 |
| 43.4 |
| 41.8 |
| 40.0 |
| 35.8 |
| 32.0 |

| ppm (±0.2) |
| --- |
| 28.1 |
| 25.1 |
| 17.5 |

Figure 4B:
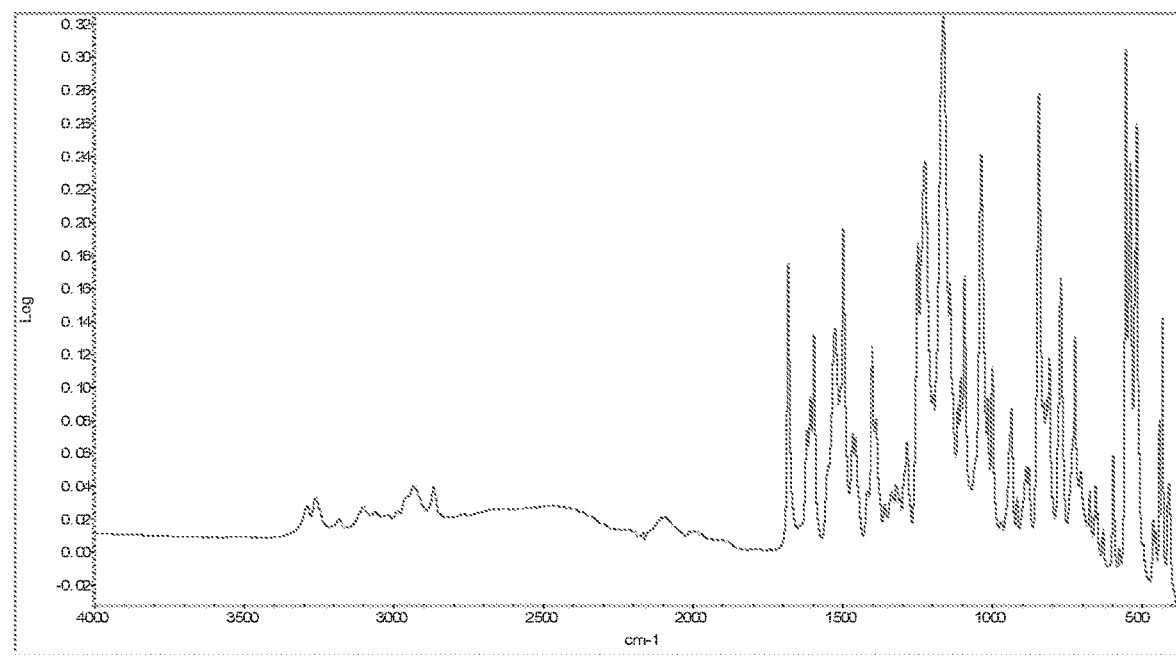
FIG. 4B depicts a FT-IR spectrum of Compound 1 MSA salt Form 1.

A FT-IR spectrum of Compound 1 MSA salt Form 1 is depicted in FIG. 4B. Compound 1 MSA salt Form 1 produces the following FT-IR peaks:

| cm$^{-1}$ (±1) |
| --- |
| 3287 |
| 3257 |
| 3179 |
| 2866 |
| 1680 |
| 1594 |
| 1495 |
| 1399 |
| 1245 |
| 1159 |
| 1090 |
| 1035 |

Figure 4C:
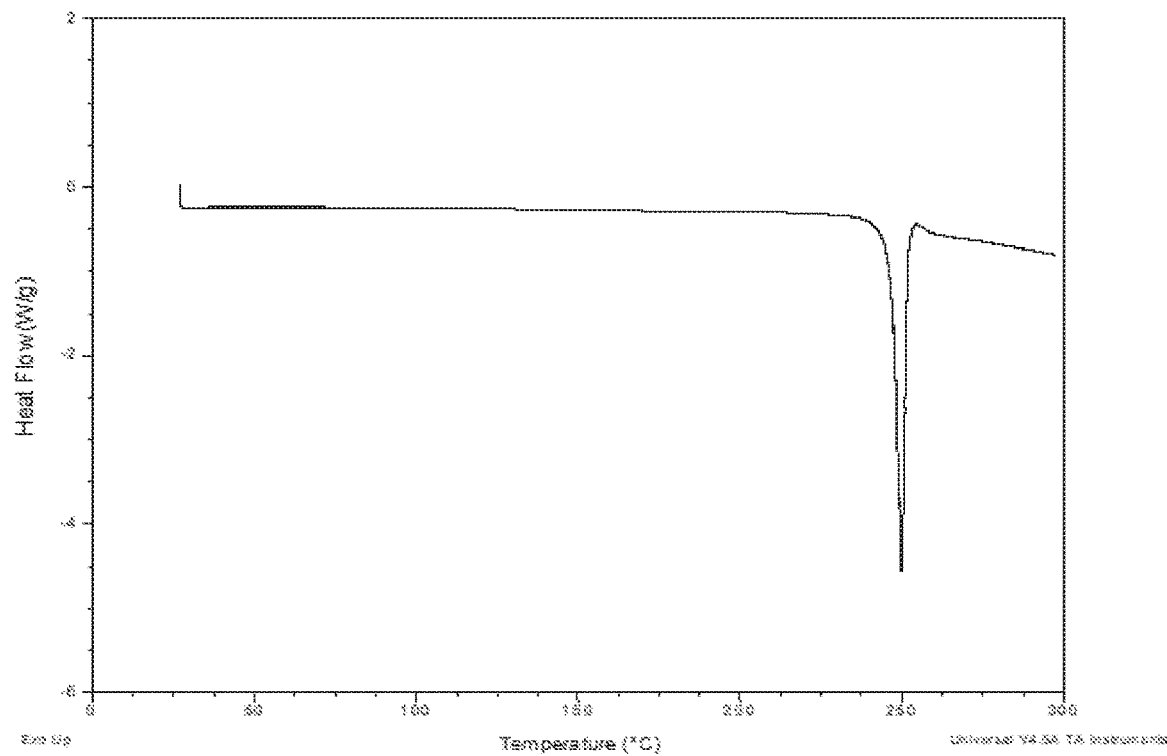
FIG. 4C depicts a DSC thermogram of Compound 1 MSA salt Form 1.

A DSC thermogram of Compound 1 MSA salt Form 1 is depicted in FIG. 4C. The DSC thermogram of Compound 1 Methanesulfonic Acid Form 1 indicates a variable endothermic transition at ~245-249° C., corresponding to melt with decomposition. Compound 1 MSA Salt Form 1 is a crystalline anhydrous material with a melting and decomposition of about 245-249° C. (onset) (based on endotherm of DSC).

Figure 4D:
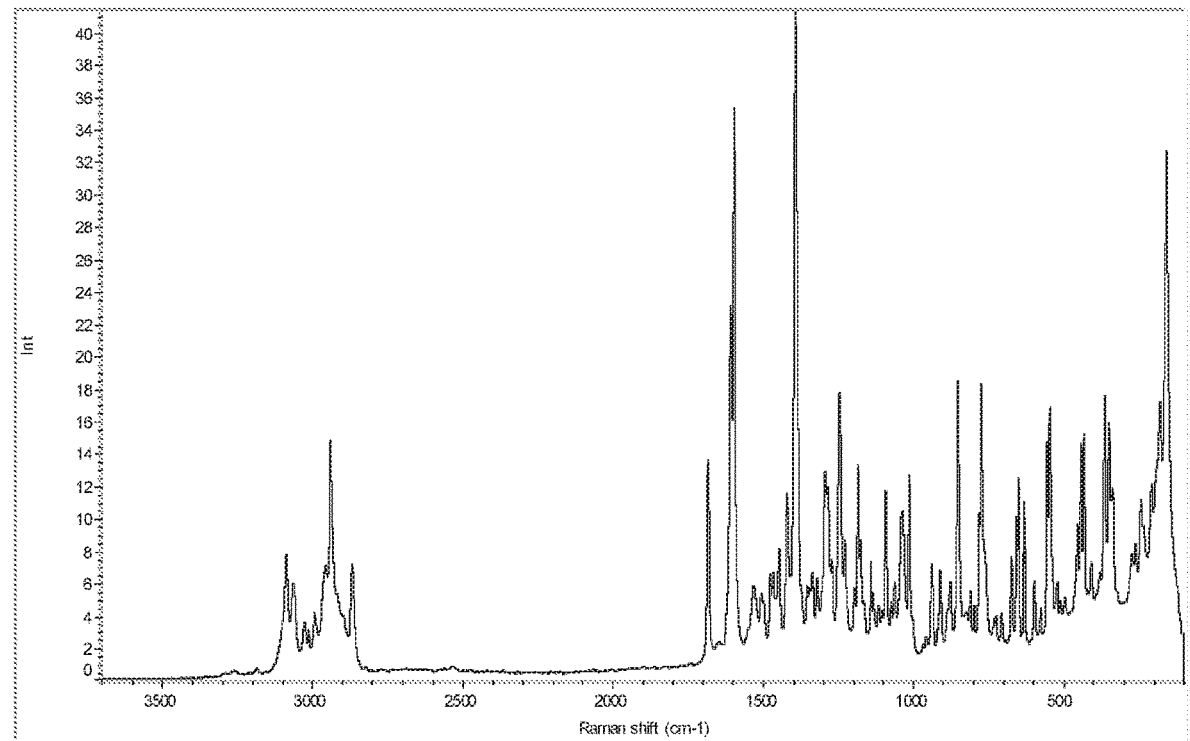
FIG. 4D depicts a FT-Raman spectrum of Compound 1 MSA salt form 1.

A FT-Raman spectrum of Compound 1 MSA salt Form 1 is depicted in FIG. 4D. Representative FT-Raman peaks are set forth in the following table:

| cm$^{-1}$ (±1) |
| --- |
| 153 |
| 176 |
| 204 |
| 345 |
| 360 |
| 429 |
| 439 |
| 542 |
| 551 |
| 645 |
| 769 |
| 848 |
| 1010 |
| 1181 |
| 1243 |
| 1291 |
| 1390 |
| 1593 |
| 1604 |
| 1680 |
| 2936 |

Figure 4E:
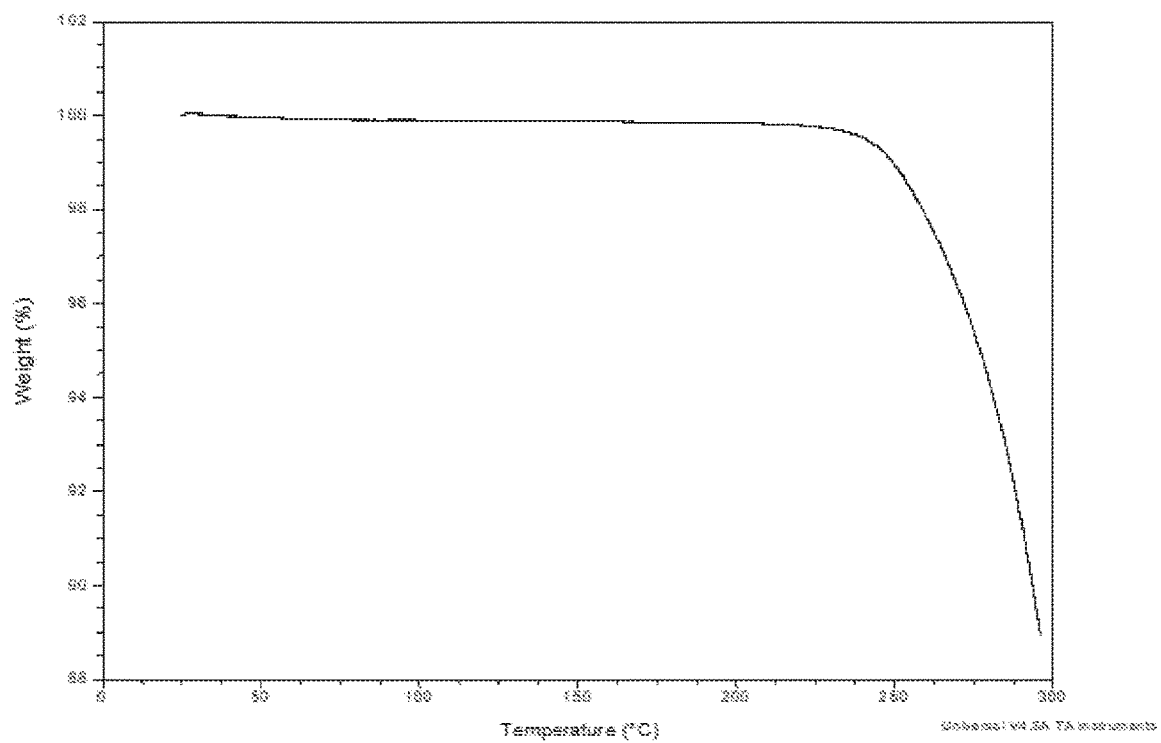
FIG. 4E depicts a TGA thermogram of Compound 1 MSA salt Form 1.

A TGA thermogram of Compound 1 MSA salt Form 1 is depicted in FIG. 4E. The TGA thermogram of Compound 1 MSA salt Form 1 is consistent with neat form, essentially free of water and residual solvents.

Figure 5:
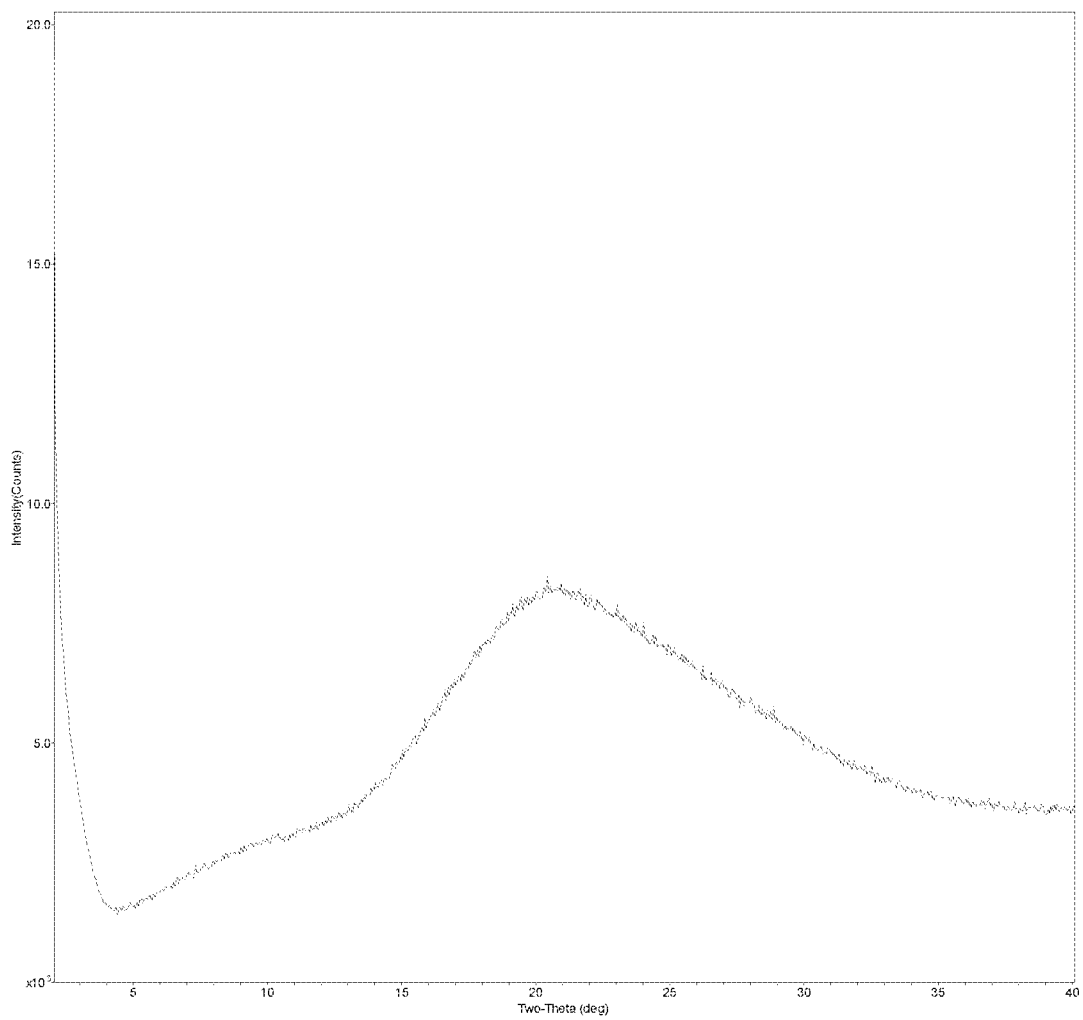
FIG. 5 depicts a powder X-ray diffractogram of amorphous Compound 1 methanesulfonic acid (MSA) salt.
Figure 5A:
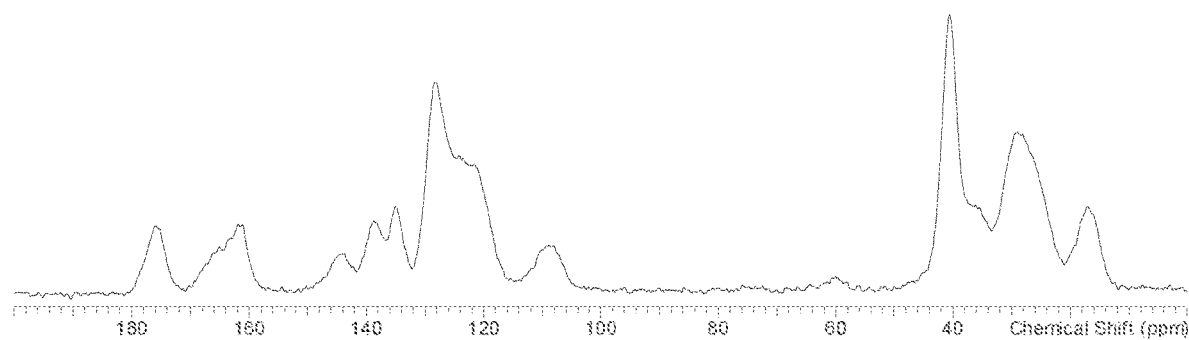
FIG. 5A depicts a ssNMR spectrum of amorphous Compound 1 MSA salt.

Also within the scope of the disclosure are amorphous forms of Compound 1 MSA salt. A PXRD of amorphous Compound 1 MSA salt is depicted in FIG. 5. A ssNMR spectrum amorphous Compound 1 MSA salt is depicted in FIG. 5A. Amorphous Compound 1 MSA salt produces the following ssNMR peaks:

| ppm (±0.2) |
| --- |
| 175.9 |
| 161.6 |
| 144.0 |
| 138.5 |
| 135.0 |
| 128.4 |
| 108.8 |
| 40.7 |
| 29.4 |
| 17.3 |

Figure 5B:
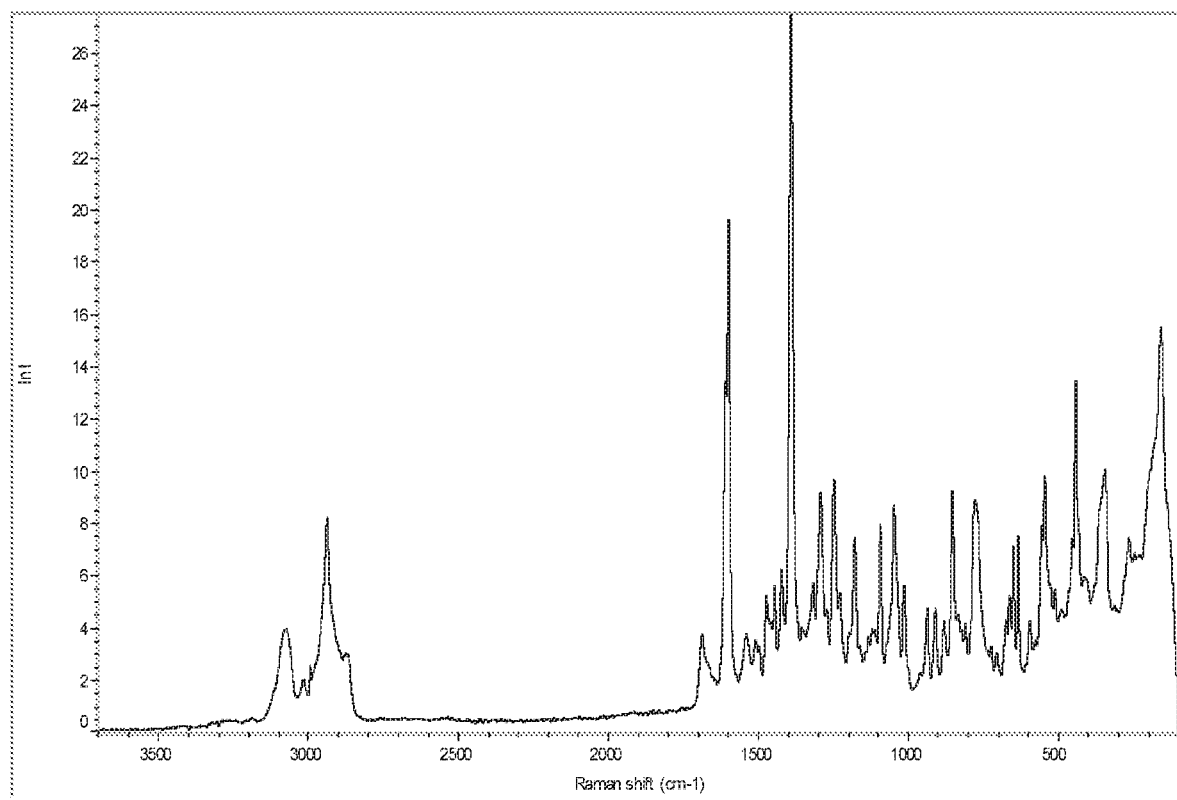
FIG. 5B depicts a FT-Raman spectrum of amorphous Compound 1 MSA salt.

A FT-Raman spectrum of Amorphous Compound 1 MSA salt is depicted in FIG. 5B. Representative peaks are presented in the below table.

| cm$^{-1}$ (±1) |
| --- |
| 152 |
| 261 |
| 340 |
| 439 |
| 449 |
| 541 |
| 552 |
| 629 |
| 644 |
| 773 |
| 848 |
| 1042 |
| 1089 |
| 1175 |
| 1245 |
| 1289 |
| 1388 |
| 1595 |
| 1605 |
| 2935 |

Compound 1 MSA salt Form 1 can be in substantially pure form, that is, having a purity of about 90% or greater, based on the weight of the compound, as determined by HPLC. For example, Compound 1 MSA salt Form 1 can have a purity of about 90, 91, 92, 93, 94, 95, 96, 97, 98, 99, or 100%. The remaining material can comprise other solid forms of Compound 1 and/or reaction impurities and/or processing impurities arising from its preparation.

Mixtures of Compound 1 MSA salt Form 1 with other solid forms of Compound 1 are also within the scope of the disclosure. In these embodiments, such mixtures can comprise less than 90%, based on the weight of the mixture, of Compound 1 MSA salt Form 1. For example, mixtures can comprise 85, 80, 75, 70, 65, 60, 55, 50, 45, 40, 35, 30, 25, 20, 15, 10, or about 5%, by weight of the mixture, of Compound 1 MSA salt Form 1.

Amorphous Compound 1 MSA salt can be in substantially pure form, that is, having a purity of about 90% or greater, based on the weight of the compound, as determined by HPLC. For example, amorphous Compound 1 MSA salt can have a purity of about 90, 91, 92, 93, 94, 95, 96, 97, 98, 99, or 100%. The remaining material can comprise other solid forms of Compound 1 and/or reaction impurities and/or processing impurities arising from its preparation.

Mixtures of amorphous Compound 1 MSA salt with other solid forms of Compound 1 are also within the scope of the disclosure. In these embodiments, such mixtures can comprise less than 90%, based on the weight of the mixture, of amorphous Compound 1 MSA salt. For example, mixtures can comprise 85, 80, 75, 70, 65, 60, 55, 50, 45, 40, 35, 30, 25, 20, 15, 10, or about 5%, by weight of the mixture, of amorphous Compound 1 MSA salt.

Compound 1 Methanesulfonic Acid Salt (MSA Salt) Hydrate

In one embodiment, the disclosure is directed to a solid form of Compound 1 methanesulfonic acid (MSA salt) that is a monohydrate. For example, the solid form of Compound 1 MSA salt monohydrate comprises about 1 molecule of water per molecule of Compound 1 MSA salt.

In a preferred aspects, the solid form of Compound 1 MSA salt monohydrate is a crystalline form of Compound 1 MSA salt monohydrate. Compound 1 MSA salt monohydrate has a desirable stability profile.

In preferred aspects of the disclosure, the Compound 1 MSA salt monohydrate is a crystalline form of Compound 1 MSA salt monohydrate, referred to herein as Compound 1 MSA salt monohydrate Form 2. Compound 1 MSA salt monohydrate Form 2 is physically stable under 95% relative humidity at room temperature for 5 days.

Compound 1 MSA salt monohydrate Form 2 can be characterized by an X-ray diffraction pattern having one peak, or at least one peak, selected from 9.3, 11.8, 14.3, 15.6, 17.7, 20.5, 22.2, 23.2, and 24.1 degrees 2θ±0.2 degrees 2θ. Compound 1 MSA salt monohydrate Form 2 can also be characterized by an X-ray diffraction pattern having two peaks selected from 9.3, 11.8, 14.3, 15.6, 17.7, 20.5, 22.2, 23.2, and 24.1 degrees 2θ±0.2 degrees 2θ. Compound 1 MSA salt monohydrate Form 2 can also be characterized by an X-ray diffraction pattern having three peaks selected from 9.3, 11.8, 14.3, 15.6, 17.7, 20.5, 22.2, 23.2, and 24.1 degrees 2θ±0.2 degrees 2θ. Compound 1 MSA salt monohydrate Form 2 can also be characterized by an X-ray diffraction pattern having four peaks selected from 9.3, 11.8, 14.3, 15.6, 17.7, 20.5, 22.2, 23.2, and 24.1 degrees 2θ±0.2 degrees 2θ. Compound 1 MSA salt monohydrate Form 2 can also be characterized by an X-ray diffraction pattern having five peaks selected from 9.3, 11.8, 14.3, 15.6, 17.7, 20.5, 22.2, 23.2, and 24.1 degrees 2θ±0.2 degrees 2θ. Compound 1 MSA salt monohydrate Form 2 can also be characterized by an X-ray diffraction pattern having six peaks selected from 9.3, 11.8, 14.3, 15.6, 17.7, 20.5, 22.2, 23.2, and 24.1 degrees 2θ±0.2 degrees 2θ. Compound 1 MSA salt monohydrate Form 2 can also be characterized by an X-ray diffraction pattern having seven peaks selected from 9.3, 11.8, 14.3, 15.6, 17.7, 20.5, 22.2, 23.2, and 24.1 degrees 2θ±0.2 degrees 2θ. Compound 1 MSA salt monohydrate Form 2 can also be characterized by an X-ray diffraction pattern having eight peaks selected from 9.3, 11.8, 14.3, 15.6, 17.7, 20.5, 22.2, 23.2, and 24.1 degrees 2θ±0.2 degrees 2θ. Compound 1 MSA salt monohydrate Form 2 can also be characterized by an X-ray diffraction pattern having peaks at 9.3, 11.8, 14.3, 15.6, 17.7, 20.5, 22.2, 23.2, and 24.1 degrees 2θ±0.2 degrees 2θ.

Diffraction peak positions for Compound 1 MSA salt monohydrate Form 2, at room temperature, based on a high quality pattern collected with a diffractometer (CuKα) with a spinning capillary with 2θ calibrated with a NIST, or other suitable standard, are shown in Table 10 and Table 10A.

TABLE 10

Characteristic diffraction peak positions for
Compound 1 MSA salt monohydrate Form 2
degrees 2θ ± 0.2

9.3
11.8

TABLE 10-continued

Characteristic diffraction peak positions for
Compound 1 MSA salt monohydrate Form 2
degrees 2θ ± 0.2

14.3
15.6
17.7
20.5
22.2
23.2
24.1

TABLE 10A

Peak Listing for Compound 1 MSA salt monohydrate Form 2
degrees 2θ ± 0.2

9.3
9.6
10.8
11.8
12.6
13.6
14.3
15.6
16.0
16.7
16.9
17.7
18.6
19.4
19.9
20.5
21.0
21.3
21.7
22.2
22.6
23.2
23.8
24.1
24.8
25.9
26.3
26.9
27.2
28.1
29.1

Compound 1 MSA salt monohydrate Form 2 can be characterized by an X ray diffraction pattern at least one peak selected from the peaks listed in Table 10A.

Figure 6:
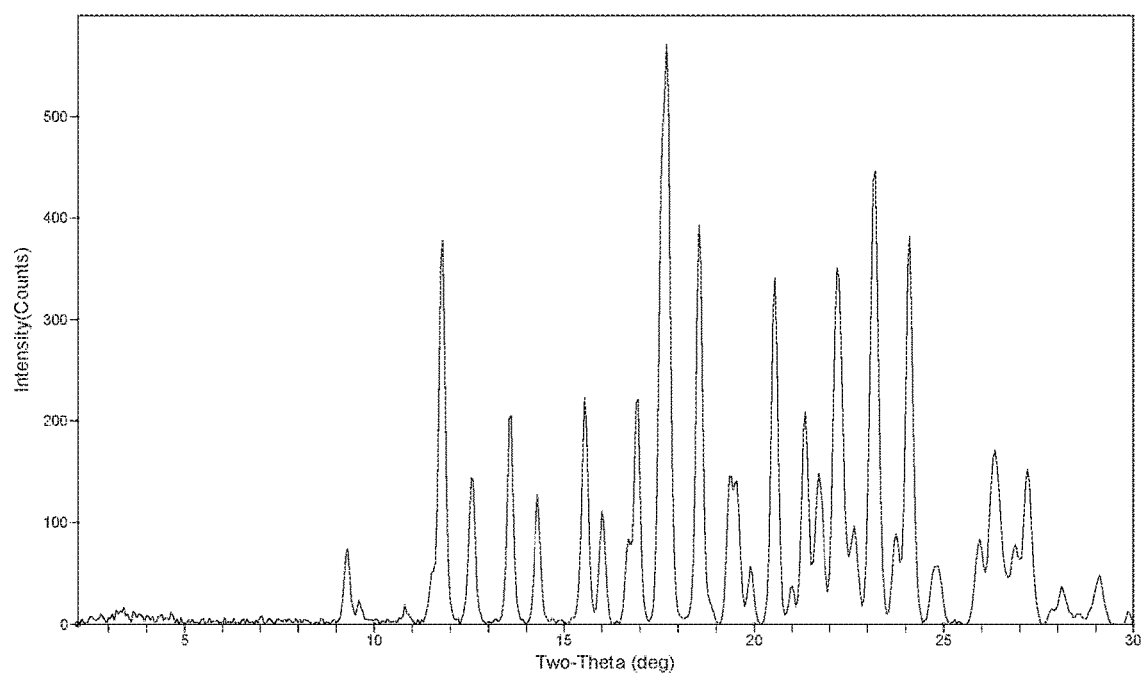
FIG. 6 depicts a powder X-ray diffractogram of Compound 1 MSA salt monohydrate Form 2.

Compound 1 MSA salt monohydrate Form 2 can also be characterized by an X-ray diffraction pattern substantially as depicted in FIG. 6. The single crystal structure of Compound 1 MSA salt hydrate Form 2 was determined successfully. The crystal system is orthorhombic and the space group is P212121. The cell parameters and calculated volume are: a=10.44447(13) Å, b=12.99925(13) Å, c=18.94899(14) Å, α=90°, β=90°, γ=90°, V=2572.71(5) Å$^3$. The formula weight is 525.02 g mol-1 with Z=4, resulting in a calculated density of 1.355 g cm$^3$. Compound 1 MSA Salt monohydrate Form 2 is a monohydrate of the Compound 1 mesylate (MSA) salt. The XRPD pattern of Compound 1 MSA salt monohydrate Form 2 indicated the material was composed of a crystalline material.

Figure 6A:
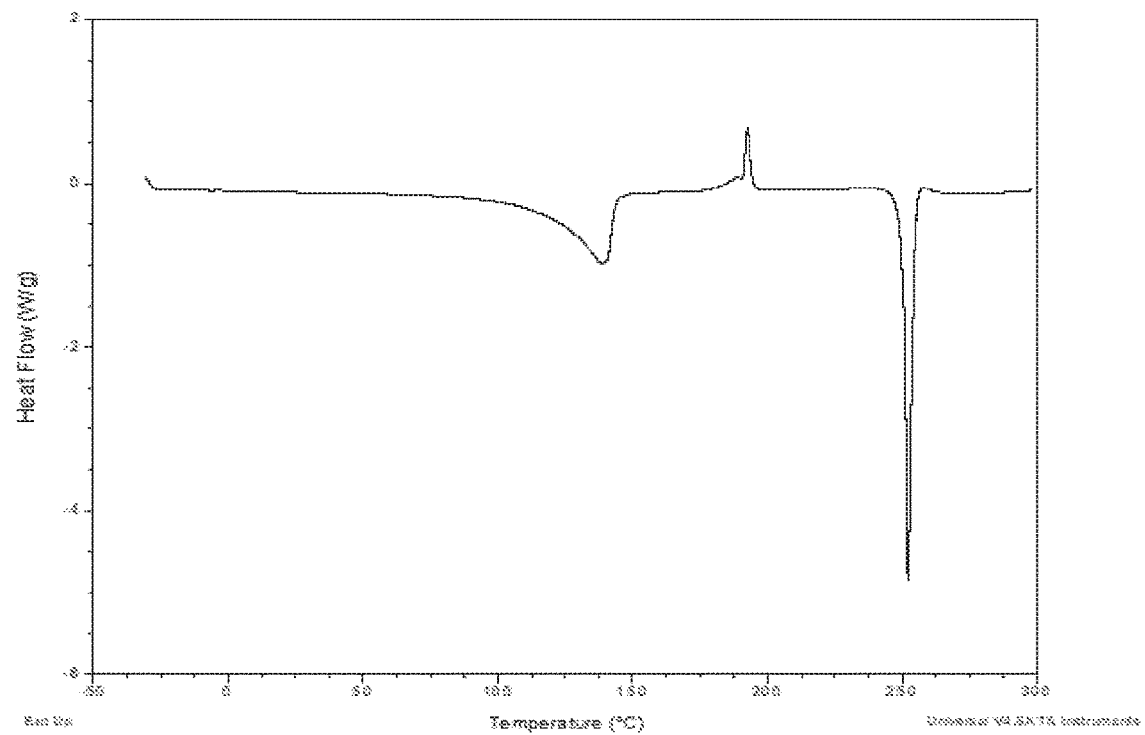
FIG. 6A depicts a DSC thermogram of Compound 1 MSA salt monohydrate Form 2.

A DSC thermogram of Compound 1 MSA salt monohydrate Form 2 is depicted in FIG. 6A.

Figure 6B:
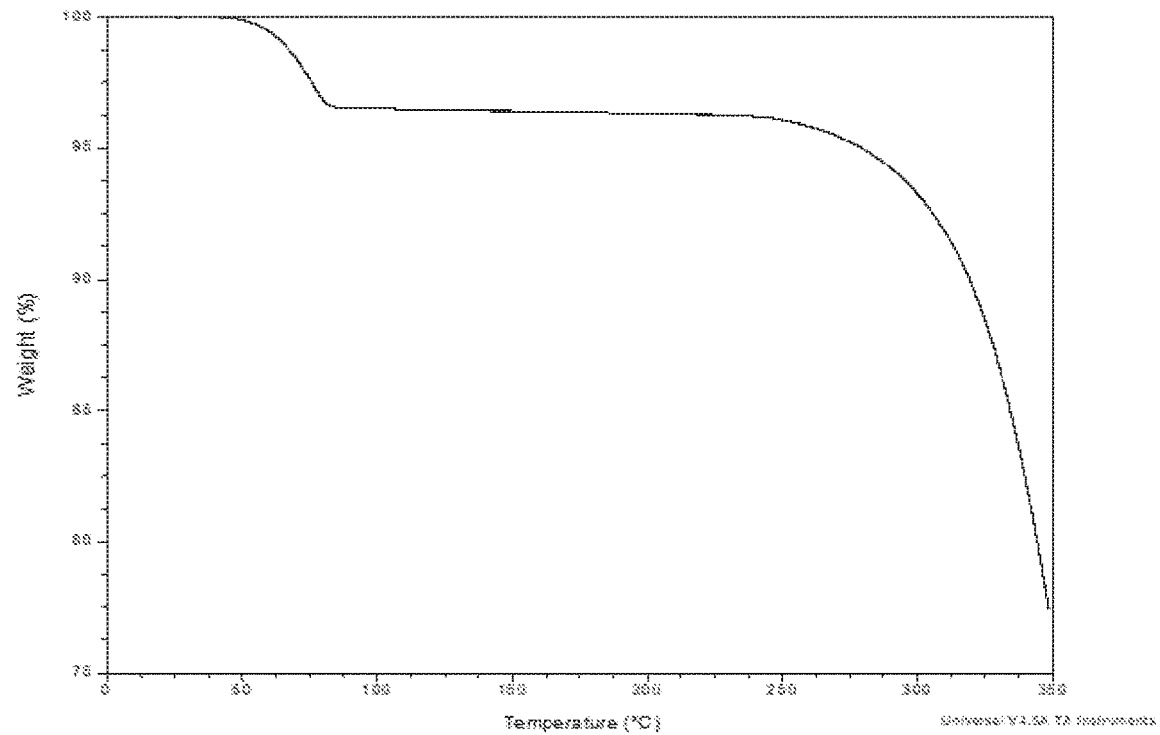
FIG. 6B depicts a TGA thermogram of Compound 1 MSA salt monohydrate Form 2.

A TGA thermogram of of Compound 1 MSA salt monohydrate Form 2 is depicted in FIG. 6B.

TGA data of Compound 1 MSA Salt monohydrate Form 2 indicated about 3.5% weight loss from up to approximately 100° C. Weight loss corresponds to approximately one mole of water per mole of API.

DSC data of Compound 1 MSA Salt monohydrate Form 2 indicated a broad endotherm was observed in the range ca. 90-150° C. which corresponds to dehydration of Compound 1 MSA Salt monohydrate Form 2, as observed in the TGA.

Compound 1 MSA monohydrate Form 2 can be in substantially pure form, that is, having a purity of about 90% or greater, based on the weight of the compound, as determined by HPLC. For example, Compound 1 MSA monohydrate Form 2 can have a purity of about 90, 91, 92, 93, 94, 95, 96, 97, 98, 99, or 100%. The remaining material can comprise other solid forms of Compound 1 and/or reaction impurities and/or processing impurities arising from its preparation.

Mixtures of Compound 1 MSA monohydrate Form 2 with other solid forms of Compound 1 are also within the scope of the disclosure. In these embodiments, such mixtures can comprise less than 90%, based on the weight of the mixture, of Compound 1 MSA monohydrate Form 2. For example, mixtures can comprise 85, 80, 75, 70, 65, 60, 55, 50, 45, 40, 35, 30, 25, 20, 15, 10, or about 5%, by weight of the mixture, of Compound 1 MSA monohydrate Form 2.

Samples of the crystalline forms described herein (e.g., Compound 1 free base Form 4, Compound 1 free base hydrate Form 2, Compound 1 MSA salt Form 1, Compound 1 MSA salt monohydrate Form 2) may be provided with substantially pure phase homogeneity, indicating the presence of a dominant amount of a single crystalline form and optionally minor amounts of one or more other crystalline forms. The presence of more than one crystalline form in a sample may be determined by techniques such as powder X-ray diffraction (PXRD) or solid state nuclear magnetic resonance spectroscopy (ssNMR). For example, the presence of extra peaks in the comparison of an experimentally measured PXRD pattern with a simulated PXRD pattern may indicate more than one crystalline form in the sample. The simulated PXRD may be calculated from single crystal X-ray data, see Smith, D. K., A FORTRAN Program for Calculating X-Ray Powder Diffraction Patterns, Lawrence Radiation Laboratory, Livermore, Calif., UCRL-7196 (April 1963). Preferably, the crystalline form has substantially pure phase homogeneity as indicated by 10% or less, preferably 5% or less, and more preferably 2% or less of the total peak area in the experimentally measured PXRD pattern arising from the extra peaks that are absent from the simulated XRPD pattern. Most preferred is a crystalline form having substantially pure phase homogeneity with 1% or less of the total peak area in the experimentally measured PXRD pattern arising from the extra peaks that are absent from the simulated PXRD pattern.

The various solid forms described herein may be distinguishable from one another through the use of various analytical techniques known to one of ordinary skill in the art. Such techniques include, but are not limited to, solid state nuclear magnetic resonance (ssNMR) spectroscopy, X-ray powder diffraction (PXRD), differential scanning calorimetry (DSC), and/or thermogravimetric analysis (TGA).

One of ordinary skill in the art will appreciate that an X-ray diffraction pattern may be obtained with a measurement error that is dependent upon the measurement conditions employed. In particular, it is generally known that intensities in an X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about ±0.2 degrees 2θ, and such degree of measurement error should be taken into account as pertaining to the aforementioned diffraction angles. Consequently, it is to be understood that the crystal forms of the instant invention are not limited to the crystalline forms that provide X-ray diffraction patterns completely identical to the X-ray diffraction patterns depicted in the accompanying Figures disclosed herein. Any crystalline forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

The solid forms of Compound 1 (and solid forms of its hydrates and salt forms) described herein may be formulated into pharmaceutical compositions and/or employed in therapeutic and/or prophylactic methods. These methods include, but are not limited to, the administration of solid forms of Compound 1, solid forms of Compound 1 hydrate (including Compound 1 monohydrate), solid forms of Compound 1 MSA salt, and solid forms of Compound 1 MSA salt hydrate, alone or in combination with one or more other pharmaceutically active agents, including agents that may be useful in the treatment of the disorders described herein.

Therapeutic Applications

The compounds and pharmaceutical compositions of the present invention are useful in treating or preventing any disease or conditions that are sensitive to enzymatic activity of IDO. These include viral and other infections (e.g., skin infections, GI infection, urinary tract infections, genitourinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the patient. In certain embodiments, the compound or pharmaceutical composition is administered orally. In other embodiments, the compound or pharmaceutical composition is administered parenterally.

Compounds of the invention can modulate activity of the enzyme indoleamine-2,3-dioxygenase (IDO). The term "modulate" is meant to refer to an ability to increase or decrease activity of an enzyme or receptor. Accordingly, compounds of the invention can be used in methods of modulating IDO by contacting the enzyme with any one or more of the compounds or compositions described herein. In some embodiments, compounds of the present invention can act as inhibitors of IDO. In further embodiments, the compounds of the invention can be used to modulate activity of IDO in cell or in an individual in need of modulation of the enzyme by administering a modulating (e.g., inhibiting) amount of a compound of the invention.

Compound 1 can inhibit activity of the enzyme indoleamine-2,3-dioxygenase (IDO). For example, Compound 1 can be used to inhibit activity of IDO in cell or in an individual in need of modulation of the enzyme by administering an inhibiting amount of Compound 1.

The present invention further provides methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of Compound 1 in a composition provided herein. Methods of measuring tryptophan levels and tryptophan degradation are routine in the art.

The present invention further provides methods of inhibiting immunosuppression such as IDO-mediated immunosuppression in a patient by administering to the patient an effective amount of Compound 1 as recited herein. IDO-mediated immunosuppression has been associated with, for example, cancers, tumor growth, metastasis, viral infection, and viral replication.

The present invention further provides methods of treating diseases associated with activity or expression, including abnormal activity and/or overexpression, of IDO in an individual (e.g., patient) by administering to the individual in need of such treatment a therapeutically effective amount or dose of a solid form of Compound 1 (or a hydrate or salt thereof) of the present invention or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosus.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a solid form of Compound 1 of the disclosure into a sample containing a cellular or purified preparation containing the IDO enzyme.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity.

Types of cancers that may be treated with the solid forms and compositions of this disclosure include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmacytoma.

Thus, according to another embodiment, the invention provides a method of treating an autoimmune disease by providing to a patient in need thereof a solid form of a compound or composition of the present invention. Examples of such autoimmune diseases include, but are not limited to, collagen diseases such as rheumatoid arthritis, systemic lupus erythematosus, Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membranoproliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barré syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

One or more additional pharmaceutical agents or treatment methods such as, for example, anti-viral agents, chemotherapeutics or other anticancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of the present invention for treatment of IDO-associated diseases, disorders or conditions. The agents can be combined with the present compounds in a single dosage form, or the agents can be administered simultaneously or sequentially as separate dosage forms.

Suitable chemotherapeutic or other anticancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of the present invention include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY®. Compounds according to the invention may also be combined with immunotherapy drugs, including cytokines such as interferon alpha, interleukin 2, and tumor necrosis factor (TNF) in the treatment of melanoma.

Compounds of the invention may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the invention, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

Suitable chemotherapeutic or other anticancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anticancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anticancer agent(s) include antibody therapeutics such as trastuzumab (HERCEPTIN®), antibodies to costimulatory molecules such as CTLA-4, 4-1BB and PD-1, or antibodies to cytokines (IL-10 or TGF-β).

Other anticancer agents also include those that block immune cell migration such as antagonists to chemokine receptors, including CCR2 and CCR4.

Other anticancer agents also include those that augment the immune system such as adjuvants or adoptive T cell transfer.

Anticancer vaccines include dendritic cells, synthetic peptides, DNA vaccines and recombinant viruses.

The pharmaceutical compositions of the disclosure may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., Clin. Cancer Res., 1:1311-1318 (1995)], and Abgenix: ABX-EGF); (iii) her-2/neu receptor inhibitors such as farnesyl transferase inhibitors (FTI) such as, for example, L-744,832 (Kohl et al., Nat. Med., 1(8):792-797 (1995)); (iv) inhibitors of Akt family kinases or the Akt pathway, such as, for example, rapamycin (see, for example, Sekulic et al., Cancer Res., 60:3504-3513 (2000)); (v) cell cycle kinase inhibitors such as, for example, flavopiridol and UCN-O1 (see, for example, Sausville, Curr. Med. Chem. Anti-Canc. Agents, 3:47-56 (2003)); and (vi) phosphatidyl inositol kinase inhibitors such as, for example, LY294002 (see, for example, Vlahos et al., J Biol. Chem., 269:5241-5248 (1994)). Alternatively, at least one STI and at least one IDO inhibitor may be in separate pharmaceutical compositions. In a specific embodiment of the present invention, at least one IDO inhibitor (such as Compound 1 or a solid form thereof, or a solid form of a hydrate or salt thereof) and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The present invention further provides a pharmaceutical composition for the treatment of a chronic viral infection in a patient comprising at least one IDO inhibitor (such as Compound 1 or a solid form of a hydrate or salt thereof), optionally, at least one chemotherapeutic drug, and, optionally, at least one antiviral agent, in a pharmaceutically acceptable carrier. The pharmaceutical compositions may include at least one IDO inhibitor of the instant invention in addition to at least one established (known) IDO inhibitor. In a specific embodiment, at least one of the IDO inhibitors of the pharmaceutical composition is Compound 1, or a solid form thereof or a solid form of a hydrate or salt thereof).

Also provided is a method for treating a chronic viral infection in a patient by administering an effective amount of the above pharmaceutical composition.

In a specific embodiment of the present invention, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, Coxsackie virus, human immunodeficiency virus (HIV). Notably, parasitic infections (e.g., malaria) may also be treated by the above methods wherein compounds known to treat the parasitic conditions are optionally added in place of the antiviral agents.

In yet another embodiment, the pharmaceutical compositions comprising at least one IDO inhibitor of the instant disclosure may be administered to a patient to prevent arterial restenosis, such as after balloon endoscopy or stent placement. In a particular embodiment, the pharmaceutical composition further comprises at least one taxane (e.g., paclitaxel (Taxol); see, e.g., Scheller et al., *Circulation*, 110:810-814 (2004)).

Suitable antiviral agents contemplated for use in combination with the solid forms of the present invention can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-I0652; emtricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfinavir (AG-1343); amprenavir (141W94); lasinavir (BMS-234475); DMP-450; BMS-232623; ABT-378; and AG-1549. Other antiviral agents include hydroxyurea, ribavirin, IL-2, IL-12, pentafuside and Yissum Project No. 11607.

Combination with an Immuno-Oncology Agent

Further provided herein are methods of treatment wherein a solid form of Compound 1, or a solid form of a hydrate or salt of Compound 1, is administered with one or more immuno-oncology agents. The immuno-oncology agents used herein, also known as cancer immunotherapies, are effective to enhance, stimulate, and/or upregulate immune responses in a subject.

In one aspect, the solid form of Compound 1, or the solid form of the hydrate or salt of Compound 1, is sequentially administered prior to administration of the immuno-oncology agent. In another aspect, the solid form of Compound 1, or the solid form of the hydrate or salt of Compound 1, is administered concurrently with the immunology-oncology agent. In yet another aspect, the Compound 1, or the solid form of the hydrate or salt of Compound 1, is sequentially administered after administration of the immuno-oncology agent.

In another aspect, the solid form of Compound 1, or the solid form of the hydrate or salt of Compound 1, may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fnl4, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In one aspect, T cell responses can be stimulated by a combination of the solid form of Compound 1, or the solid form of the hydrate or salt of Compound 1, and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with the solid form of Compound 1, or the solid form of the hydrate or salt of Compound 1, for the treatment of cancer include antagonists of inhibitory receptors on NK cells or agonists of activating receptors on NK cells. For example, the solid form of Compound 1, or the solid form of the hydrate or salt of Compound 1, can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO 11/70024, WO 11/107553, WO 11/131407, WO 13/87699, WO 13/119716, WO 13/132044) or FPA-008 (WO 11/140249, WO 13/169264, WO 14/036357).

In another aspect, the solid form of Compound 1, or the solid form of the hydrate or salt of Compound 1, can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY® (ipilimumab) or tremelimumab.

In another aspect, the immuno-oncology agent is a PD-1 antagonist, such as an antagonistic PD-1 antibody. Suitable PD-1 antibodies include, for example, OPDIVO® (nivolumab), KEYTRUDA® (pembrolizumab), or MEDI-0680 (AMP-514; WO 2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO 2010/077634), durvalumab (MED14736), BMS-936559 (WO 2007/005874), and MSB0010718C (WO 2013/79174).

In another aspect, the immuno-oncology agent is a LAG-3 antagonist, such as an antagonistic LAG-3 antibody. Suitable LAG3 antibodies include, for example, BMS-986016 (WO 10/19570, WO 14/08218), or IMP-731 or IMP-321 (WO 08/132601, WO 09/44273).

In another aspect, the immuno-oncology agent is a CD137 (4-1BB) agonist, such as an agonistic CD137 antibody. Suitable CD137 antibodies include, for example, urelumab and PF-05082566 (WO 12/32433).

In another aspect, the immuno-oncology agent is a GITR agonist, such as an agonistic GITR antibody. Suitable GITR antibodies include, for example, BMS-986153, BMS-986156, TRX-518 (WO 06/105021, WO 09/009116) and MK-4166 (WO 11/028683).

In another aspect, the immuno-oncology agent is an IDO antagonist. Suitable IDO antagonists include, for example, INCB-024360 (WO 2006/122150, WO 07/75598, WO 08/36653, WO 08/36642), indoximod, or NLG-919 (WO 09/73620, WO 09/1156652, WO 11/56652, WO 12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO 06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO 11/109400).

The present invention also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions and Dosing

The disclosure also provides pharmaceutically acceptable compositions which comprise a therapeutically effective amount of one or more of the solid forms described herein, formulated together with one or more pharmaceutically acceptable carriers (additives) and/or diluents, and optionally, one or more additional therapeutic agents.

The solid forms of the disclosure can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; buccally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, Jr., L. V. et al., *Remington: The Science and Practice of Pharmacy* (2 Volumes), 22nd Edition, Pharmaceutical Press (2012).

The dosage regimen for solid forms of the present disclosure will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The solid forms of the disclosure are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 mg to about 2000 mg of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, solid forms of the present disclosure can be used alone, in combination with other compounds of the invention, or in combination with one or more other therapeutic agent(s), e.g., an anticancer agent or other pharmaceutically active material.

Regardless of the route of administration selected, the solid forms of the present disclosure, are formulated into pharmaceutically acceptable dosage forms by conventional methods known to those of skill in the art.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient.

The selected dosage level will depend upon a variety of factors including the activity of the compound of the present disclosure employed, the route of administration, the time of administration, the rate of excretion or metabolism of the compound, the rate and extent of absorption, the duration of the treatment, other drugs, compounds and/or materials used in combination with the compound, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of compound will be that amount of compound which is the lowest dose effective to produce a therapeutic effect. Such an effective dose will generally depend upon the factors described above.

If desired, the effective daily dose of the compound may be administered as two, three, four, five, six or more sub-doses administered separately at appropriate intervals throughout the day, optionally, in unit dosage forms. In certain aspects of the invention, dosing is one administration per day.

While it is possible for a compound of the present disclosure to be administered alone, it is preferable to administer the compound as a pharmaceutical formulation (composition).

Definitions

Some aspects of the disclosure are directed to crystalline forms. Crystalline forms produce an X-ray diffraction pattern with sharp maxima.

As used herein "amorphous" refers to a solid form of a molecule, and/or ions that is not crystalline. An amorphous solid does not display an X-ray diffraction pattern with sharp maxima.

As used herein, "hydrate" refers to a crystalline form of a molecule that further comprises water incorporated into the crystalline structure. The water molecules in the hydrate may be present in a regular arrangement and/or a non-ordered arrangement. The hydrate may comprise either a stoichiometric or nonstoichiometric amount of the water molecules.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Aspects

Aspect 1. Crystalline (R)-N-(4-chlorophenyl)-2-((1S,4S)-4-(6-fluoroquinolin-4-yl)cyclohexyl)propanamide Form 4.

Aspect 2. The crystalline (R)-N-(4-chlorophenyl)-2-((1S,4S)-4-(6-fluoroquinolin-4-yl)cyclohexyl)propanamide Form 4 of Aspect 1, characterized by a powder X-ray diffraction pattern comprising at least one peak selected from 7.6, 12.0, 13.5, 14.4, 17.6, 20.1, 20.7, and 22.0 degrees 2θ±0.2 degrees 2θ.

Aspect 3. The crystalline (R)-N-(4-chlorophenyl)-2-((1S,4S)-4-(6-fluoroquinolin-4-yl)cyclohexyl)propanamide Form 4 of Aspect 1, characterized by a powder X-ray diffraction pattern comprising two peaks selected from 7.6, 12.0, 13.5, 14.4, 17.6, 20.1, 20.7, and 22.0 degrees 2θ±0.2 degrees 2θ.

Aspect 4. The crystalline (R)-N-(4-chlorophenyl)-2-((1S,4S)-4-(6-fluoroquinolin-4-yl)cyclohexyl)propanamide Form 4 of Aspect 1, characterized by a powder X-ray diffraction pattern comprising three peaks selected from 7.6, 12.0, 13.5, 14.4, 17.6, 20.1, 20.7, and 22.0 degrees 2θ±0.2 degrees 2θ.

Aspect 5. The crystalline (R)-N-(4-chlorophenyl)-2-((1S,4S)-4-(6-fluoroquinolin-4-yl)cyclohexyl)propanamide Form 4 of Aspect 1, characterized by a powder X-ray diffraction pattern comprising four peaks selected from 7.6, 12.0, 13.5, 14.4, 17.6, 20.1, 20.7, and 22.0 degrees 2θ±0.2 degrees 2θ.

Aspect 6. Crystalline (R)-N-(4-chlorophenyl)-2-((1S,4S)-4-(6-fluoroquinolin-4-yl)cyclohexyl)propanamide mono-hydrate Form 2.

Aspect 7. The crystalline (R)-N-(4-chlorophenyl)-2-((1S,4S)-4-(6-fluoroquinolin-4-yl)cyclohexyl)propanamide monohydrate Form 2 of Aspect 6, characterized by a powder X-ray diffraction pattern comprising at least one peak selected from 9.4, 12.4, 17.2, 17.6, 20.1, 21.1, and 21.6 degrees 2θ±0.2 degrees 2θ.

Aspect 8. The crystalline (R)-N-(4-chlorophenyl)-2-((1S,4S)-4-(6-fluoroquinolin-4-yl)cyclohexyl)propanamide monohydrate Form 2 of Aspect 6, characterized by a powder X-ray diffraction pattern comprising two peaks selected from 9.4, 12.4, 17.2, 17.6, 20.1, 21.1, and 21.6 degrees 2θ±0.2 degrees 2θ.

Aspect 9. The crystalline (R)-N-(4-chlorophenyl)-2-((1S,4S)-4-(6-fluoroquinolin-4-yl)cyclohexyl)propanamide monohydrate Form 2 of Aspect 6, characterized by a powder X-ray diffraction pattern comprising three peaks selected from 9.4, 12.4, 17.2, 17.6, 20.1, 21.1, and 21.6 degrees 2θ±0.2 degrees 2θ.

Aspect 10. The crystalline (R)-N-(4-chlorophenyl)-2-((1S,4S)-4-(6-fluoroquinolin-4-yl)cyclohexyl)propanamide monohydrate Form 2 of Aspect 6, characterized by a powder X-ray diffraction pattern comprising four peaks selected from 9.4, 12.4, 17.2, 17.6, 20.1, 21.1, and 21.6 degrees 2θ±0.2 degrees 2θ.

Aspect 11. Crystalline (R)-N-(4-chlorophenyl)-2-((1S,4S)-4-(6-fluoroquinolin-4-yl)cyclohexyl)propanamide methanesulfonic acid Form 1.

Aspect 12. The crystalline (R)-N-(4-chlorophenyl)-2-((1S,4S)-4-(6-fluoroquinolin-4-yl)cyclohexyl)propanamide methanesulfonic acid Form 1 of Aspect 11, characterized by a powder X-ray diffraction pattern comprising at least one peak selected from 12.2, 12.6, 13.4, 14.8, 16.4, 16.8, 19.6, and 24.0 degrees 2θ±0.2 degrees 2θ.

Aspect 13. The crystalline (R)-N-(4-chlorophenyl)-2-((1S,4S)-4-(6-fluoroquinolin-4-yl)cyclohexyl)propanamide methanesulfonic acid Form 1 of Aspect 11, characterized by a powder X-ray diffraction pattern comprising two peaks selected from 12.2, 12.6, 13.4, 14.8, 16.4, 16.8, 19.6, and 24.0 degrees 2θ±0.2 degrees 2θ.

Aspect 14. The crystalline (R)-N-(4-chlorophenyl)-2-((1S,4S)-4-(6-fluoroquinolin-4-yl)cyclohexyl)propanamide methanesulfonic acid Form 1 of Aspect 11, characterized by a powder X-ray diffraction pattern comprising three peaks selected from 12.2, 12.6, 13.4, 14.8, 16.4, 16.8, 19.6, and 24.0 degrees 2θ±0.2 degrees 2θ.

Aspect 15. The crystalline (R)-N-(4-chlorophenyl)-2-((1S,4S)-4-(6-fluoroquinolin-4-yl)cyclohexyl)propanamide methanesulfonic acid Form 1 of Aspect 11, characterized by a powder X-ray diffraction pattern comprising four peaks selected from 12.2, 12.6, 13.4, 14.8, 16.4, 16.8, 19.6, and 24.0 degrees 2θ±0.2 degrees 2θ.

Aspect 16. Amorphous (R)-N-(4-chlorophenyl)-2-((1S,4S)-4-(6-fluoroquinolin-4-yl)cyclohexyl)propanamide methanesulfonic acid.

Aspect 17. A pharmaceutical composition comprising
crystalline (R)-N-(4-chlorophenyl)-2-((1S,4S)-4-(6-fluoroquinolin-4-yl)cyclohexyl)propanamide Form 4;
crystalline (R)-N-(4-chlorophenyl)-2-((1S,4S)-4-(6-fluoroquinolin-4-yl)cyclohexyl)propanamide monohydrate Form 2; or
crystalline (R)-N-(4-chlorophenyl)-2-((1S,4S)-4-(6-fluoroquinolin-4-yl)cyclohexyl)propanamide methanesulfonic acid Form 1;
or a combination thereof;
and a pharmaceutically acceptable carrier.

Aspect 18. The pharmaceutical composition of Aspect 17, further comprising amorphous (R)-N-(4-chlorophenyl)-2-((1S,4S)-4-(6-fluoroquinolin-4-yl)cyclohexyl)propanamide, amorphous (R)-N-(4-chlorophenyl)-2-((1S,4S)-4-(6-fluoroquinolin-4-yl)cyclohexyl)propanamide methanesulfonic acid, or a combination thereof.

Aspect 19. The pharmaceutical composition of claim Aspect 17, further comprising amorphous (R)-N-(4-chlorophenyl)-2-((1S,4S)-4-(6-fluoroquinolin-4-yl)cyclohexyl)propanamide.

Aspect 20. A method of treating cancer in a patient in need of such treatment comprising administering to the patient a therapeutically effective amount of
crystalline (R)-N-(4-chlorophenyl)-2-((1S,4S)-4-(6-fluoroquinolin-4-yl)cyclohexyl)propanamide Form 4;
crystalline (R)-N-(4-chlorophenyl)-2-((1S,4S)-4-(6-fluoroquinolin-4-yl)cyclohexyl)propanamide monohydrate Form 2; or
crystalline (R)-N-(4-chlorophenyl)-2-((1S,4S)-4-(6-fluoroquinolin-4-yl)cyclohexyl)propanamide methanesulfonic acid Form 1;
or a combination thereof.

Aspect 21. The method of Aspect 20, wherein the cancer is a cancer of the prostate, colon, rectum, pancreas, cervix, stomach, endometrium, brain, liver, bladder, ovary, testis, head, neck, skin (including melanoma and basal carcinoma), mesothelial lining, white blood cell (including lymphoma and leukemia), esophagus, breast, muscle, connective tissue, lung (including small-cell lung carcinoma and non-small-cell carcinoma), adrenal gland, thyroid, kidney, or bone; or is glioblastoma, mesothelioma, renal cell carcinoma, gastric carcinoma, sarcoma (including Kaposi's sarcoma), choriocarcinoma, cutaneous basocellular carcinoma, or testicular seminoma.

Aspect 22. The method of Aspect 20, further comprising administration of amorphous (R)-N-(4-chlorophenyl)-2-((1S,4S)-4-(6-fluoroquinolin-4-yl)cyclohexyl)propanamide, amorphous (R)-N-(4-chlorophenyl)-2-((1S,4S)-4-(6-fluoroquinolin-4-yl)cyclohexyl)propanamide methanesulfonic acid, or a combination thereof.

Aspect 23. The method of Aspect 20, further comprising administration of an immune checkpoint inhibitor.

Aspect 24. The method of Aspect 20, wherein the immune checkpoint inhibitor is ipilimumab (YERVOY™), nivolumab (OPDIVO™), pembroluzimab (KEYTRUDA™), or a combination thereof.

Aspect 25. A method of modulating the activity of indoleamine 2,3-dioxygenase comprising
contacting the indoleamine 2,3-dioxygenase with
crystalline (R)-N-(4-chlorophenyl)-2-((1s,4S)-4-(6-fluoroquinolin-4-yl)cyclohexyl)propanamide Form 4;
crystalline (R)-N-(4-chlorophenyl)-2-((1S,4S)-4-(6-fluoroquinolin-4-yl)cyclohexyl)propanamide monohydrate Form 2; or
crystalline (R)-N-(4-chlorophenyl)-2-((1S,4S)-4-(6-fluoroquinolin-4-yl)cyclohexyl)propanamide methanesulfonic acid Form 1;
or a combination thereof;
optionally in combination with amorphous (R)-N-(4-chlorophenyl)-2-((1S,4S)-4-(6-fluoroquinolin-4-yl)cyclohexyl)propanamide, amorphous (R)-N-(4-chlorophenyl)-2-((1S,4S)-4-(6-fluoroquinolin-4-yl)cyclohexyl)propanamide methanesulfonic acid, or a combination thereof.

EXAMPLES

The following Examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Methods
Single Crystal Data

Single crystal X-ray data of Compound 1 MSA Salt, Form 1 was collected using a Bruker X8 APEX II CCD diffractometer equipped with a MICROSTAR-H microfocus rotating anode X-ray generator of monochromatic Cu Kα radiation ($\lambda$=1.54178 Å). The single crystal was at room temperature during data collection.

Single crystal X-ray data of Compound 1 Free Base monohydrate, Form 2 and Compound 1 Free Base, Form 4 were collected using a Bruker X8 Prospector Ultra diffractometer equipped with APEX II detector and I μS microfocus X-ray source of monochromatic Cu Kα radiation ($\lambda$=1.54178 Å). The single crystals were at room temperature during data collection.

Single crystal X-ray data for Compound 1 MSA salt hydrate Form 2 was collected using a Rigaku SuperNova diffractometer equipped with a Dectris Pilatus 200K detector and a micro-focus sealed tube X-ray generator of monochromatic Cu Kα radiation. The single crystal is at room temperature during data collection. Indexing and processing of the measured intensity data were carried out with the software suite CrysAlisPro 1.171.38.41r (Rigaku OD, 2015).

Indexing and processing of the measured intensity data were carried out with the APEX2 program suite (Bruker AXS, Inc., 5465 East Cheryl Parkway, Madison, Wis. 53711 USA). The final unit cell parameters were determined using the full data set. The structures were solved by direct methods and refined by full-matrix least-squares approach using the SHELXTL software package (G. M. Sheldrick, SHELXTL v6.14, Bruker AXS, Madison, Wis. USA.). Structure refinements involved minimization of the function defined by $\Sigma w(|F_o|-|F_c|)^2$, where w is an appropriate weighting factor based on errors in the observed intensities, $F_o$ is the structure factor based on measured reflections, and $F_c$ is the structure factor based on calculated reflections. Agreement between the refined crystal structure model and the experimental X-ray diffraction data is assessed by using the residual factors $R=\Sigma||F_o|-|F_c||/\Sigma|F_o|$ and $wR=[\Sigma w(|F_o|-|F_c|)^2/\Sigma w|F_o|]^{1/2}$. Difference Fourier maps were examined at all stages of refinement. All non-hydrogen atoms were refined with anisotropic thermal displacement parameters. Hydrogen atoms were generally calculated using idealized geometry, assigned isotropic temperature factors, and included in structure factor calculations with fixed parameters. There were a few exceptions where hydrogen atoms were located from the difference Fourier maps and refined isotropically, such as hydrogen atoms of water in Compound 1 Free Base Hydrate Form 2 structure, and acidic hydrogen atom of methanesulfonic acid in the Compound 1 MSA Salt Form 1 structure.

PXRD (PANalytical)

The PXRD pattern for amorphous Compound 1 free base and amorphous Compound 1 MSA salt was recorded on an Empyrean (PANalytical) X-ray powder diffractometer with Cu Kα radiation: $\lambda$=1.541 Å. The diffractometer was equipped with a ceramic tube which was set at the power level of 45 kV and 40 mA, and a RTMS PIXcel 1D detector. Incident optics consisted of a 0.02 rad soller slit; 10 mm beam mask; 1° antiscatter slit; and auto-divergence slit set to 10 mm illuminated length. Diffracted optics consisted of a 0.02 rad soller slit; auto-anti-scatter slit set to 10 mm illuminated length; Ni-K-Beta filter, and detector window of ~2.9°. Data was collected in a continuous scan mode in reflectance geometry, whilst spinning, over a 20 range of 2-40°, with a step size of 0.033-040°, and net counting time of ~317 sec/step. Greater than 200 mg of powder sample was packed in backfill sample holders.

PXRD (GADDS-NB)
Capillary

PXRD data were obtained using a Bruker C2 GADDS. The radiation was Cu Ku (40 KV, 40 mA). The sample-detector distance was 15 cm. Samples were placed in sealed glass capillaries with diameters of ≤1 mm. The capillary was rotated during data collection. Data were collected for approximately 2≤2θ≤32° with a sample exposure time of at least 1000 seconds. The resulting two dimensional diffraction arcs were integrated to create a traditional 1-dimensional PXRD pattern with a step size of 0.05 degrees 2θ in the approximate range of 2 to 32 degrees 2θ.

Differential Scanning Calorimetry (DSC)

Differential scanning calorimetry (DSC) experiments for Compound 1 Free base hydrate, Compound 1 free base, and Compound 1 MSA salt were performed using a TA Instrument—model Q2000 or Q1000. The sample (about 1-10 mg) was weighed in an aluminum pan and the weight recorded accurately to a hundredth of a milligram before transferring the sample to the DSC. The instrument was purged with nitrogen gas at 50 mL/min. Data were collected between room temperature and 300° C. at a heating rate of 10° C./min. DSC plots were generated such that the endothermic peaks pointed down.

DSC for Compound 1 MSA hydrate was performed using a TA Instruments 2920 differential scanning calorimeter. Temperature calibration was performed using NIST-traceable indium metal. The sample was placed into an aluminum DSC pan, covered with a lid, the lid was hermetically sealed and perforated with a laser pinhole and the weight was accurately recorded (3.7940 mg). A weighed aluminum pan configured as the sample pan was placed on the reference side of the cell. Analysis was performed from −30° C. to 300° C. at 10° C./min.

Thermogravimetric Analysis (TGA)

Thermal gravimetric analysis (TGA) experiments for Compound 1 free base hydrate, Compound 1 free base, and Compound 1 MSA salt were performed using a TA Instrument-model Q5000 or Q500. The sample (about 10-30 mg) was placed in a previously tarred platinum pan. The weight of the sample was measured accurately and recorded to a thousandth of a milligram by the instrument. The furnace was purged with nitrogen gas at 100 mL/min. Data were collected between room temperature and 300° C. at a heating rate of 10° C./min.

TG analysis for Compound 1 MSA salt hydrate was performed using a TA Instruments Q5000 thermogravimetric analyzer. Temperature calibration was performed using nickel and Alumel. The sample (5.6360 mg) was placed in an aluminum pan. The sample was hermetically sealed, the lid pierced, then inserted into the TG furnace. The furnace was heated under nitrogen. Analysis was performed from ambient temperature to 350° C. at 10° C./min.

Solid-State Nuclear Magnetic Resonance (ssNMR)

Carbon-13 cross polarization magic angle spinning (CP-MAS) solid-state NMR experiments were conducted on a Bruker AV III instrument operating at a proton frequency of 500 MHz. Solid samples were spun at 13 kHz in a 4 mm $ZrO_2$ rotor. The contact time was 4 milliseconds and was ramped on the proton channel from 50 to 100% (A. E. Bennett et al, *J Chem. Phys.*, 1995, 103, 6951), (G. Metz, X. Wu and S. O. Smith, *J. Magn. Reson. A.*, 1994, 110, 219-227). The relaxation delay was maintained at 5x $^1$H Ti of API, which was 20 seconds. Proton decoupling was applied using a TPPM sequence with a 4.3 microsecond pulse (58 kHz nominal bandwidth). The spectral sweep width was 300 ppm centered at 100 ppm. 2048 data points were acquired (giving a digital resolution of 36 Hz) and zero filled to 8192 prior to apodization. 2048 free induction decays were co-added. The spectra were referenced indirectly to TMS using 3-methylglutaric acid (D. Barich, E. Gorman, M. Zell, and E. Munson, *Solid State Nuc. Mag. Res.*, 2006, 30, 125-129). Approximately 80 mg of sample was used for each experiment. The temperature was set to 280K.

FT-Infra-Red

FTIR spectroscopy was performed using a IS50-ATR spectrometer with attenuated total reflectance (ATR). The spectra were collected using reflection mode with a resolution of 4 cm$^{-1}$ and 64 scans. The spectra were collected with a resolution of 4 cm$^{-1}$ and 64 scans.

FT-Raman

FT-Raman spectra were acquired at a resolution of 4 cm$^{-1}$ with 64 scans co-added, using a Nicolet iS50 FT-Raman spectrometer integrated with a high sensitivity InGaS detector. The wavelength of the laser excitation was 1064 nm. The laser power was 0.5 W.

Stability Testing Chromatographic Conditions:

VHPLC Parameters

VHPLC System: Waters AcQuity BSM or H-Class VHPLC system equipped with a Waters UV/Vis Detector Column: Ascentis Express C18, 150 mm×2.1 mm i.d., 2.7 um particle size.

Detector Wavelength: 218 nm

VHPLC detector time constrat: normal

VHPLC sampling rate: 20 Hz

VHPLC bandwidth: 1.2 nm resolution

Flow Rate: 0.5 mL/min

Injection volume 1 uL

Column temperature: 30° C.

Run time: ~14 minutes

Sample temperature: 5° C.

Mobile Phase A: water:acetonitrile:TFA (95:5:0.05)

Mobile Phase B: water: acetonitrile:TFA (5:95:0.05)

| VHPLC Gradient Program Listing | | | |
| --- | --- | --- | --- |
| | Mobile Phase Composition | | Gradient |
| Time (min) | % A | % B | Profile |
| 0 | 85 | 15 | Initial |
| 0.5 | 85 | 15 | Isocratic |
| 5.5 | 45 | 55 | Linear |
| 8.0 | 35 | 65 | Linear |
| 10 | 0 | 100 | Linear |
| 10.5 | 85 | 15 | Linear |
| 14 | 85 | 15 | Isocratic |

Typical retention time for Compound 1: retention time (min) 5.66; relative retention time (min) 1.00

Microdissolution

Microdissolution experiments were conducted in a pIon μDiss Profiler microdissolution instrument (pION μDiss Profiler) with a fiber optic UV monitoring system, as follows:

Probes: 2.5 mm probes (5 mm path length)

Volume: 15 ml

Stirring: 150 rpm

Temperature: 37° C. (solutions and instrument bath)

Blank: Instant FaSSIF/FeSSIF

Standards: 6 standard concentrations (0, 5, 15, 25, 50, 100, 200 μg/ml)

Vehicle: 10 mg/ml DMSO

Wavelength: 280 nm, baseline 450 nm

Example 1. Compound 1

Compound 1 may be prepared using the methods described in WO2016/073770, incorporated by reference herein.

Example 2: Compound 1 Free Base, Amorphous

To a 1 L round bottom flask was charged 132.0 g (R)-N-(4-chlorophenyl)-2-((1S,4S)-4-(6-fluoroquinolin-4-yl)cyclohexyl)propanamide hydrate and 610 g ethyl acetate. The slurry was heated until all solids dissolved. The solution was the concentrated to dryness under vacuum. The resulting solids were dried under vacuum at 50° C. to yield 126.0 g of (R)-N-(4-chlorophenyl)-2-((1S,4S)-4-(6-fluoroquinolin-4-yl)cyclohexyl)propanamide as a white solid in 99.6% yield.

Example 3: Compound 1 Free Base Hydrate, Form 2

To a 50 L glass-lined reactor under a blanket of nitrogen was charged 13.75 kg acetonitrile, then 2.68 kg N,N,N',N'-tetramethylchloroformamidinium hexafluorophosphate (TCFH) and rinsed with 2.0 kg acetonitrile. 2.03 Kg N-methylimidazole was added followed by 1.95 kg acetonitrile. 2.48 Kg (R)-2-((1S,4S)-4-(6-fluoroquinolin-4-yl)cyclohexyl)propanoic acid was added followed by 1.05 kg acetonitrile. The mixture was held for 0.5 h then 1.21 kg 4-chloroaniline charged followed by 1.0 kg acetonitrile. The mixture was maintained at 20° C. until the reaction was deemed complete by HPLC analysis. The solution was then heated to 60° C., and 9.25 kg water was charged. The solution was then cooled to 40° C., the mixture was aged for 1 h, seeds (32 g) were charged and rinsed with 1.15 kg 2:1 water:acetonitrile, and the resulting slurry was maintained for 1 h. The slurry was then cooled to 20° C. and 25.75 kg water was charged. The slurry was filtered and the cake was washed three times with 6.9 kg of 2:1 water:acetonitrile. The cake was dried under vacuum at 50° C. to yield 3.33 kg of (R)-N-(4-chlorophenyl)-2-((1S,4S)-4-(6-fluoroquinolin-4-yl)cyclohexyl)propanamide hydrate as a white solid in 94.1% yield.

Example 4: Compound 1 Free Base Hydrate, Form 2

250 mg of amorphous Compound 1 free base was dissolved at 40° C. to 50° C. in 2 mL of and organic solvent, for example, ethanol, acetone, acetonitrile, or tetrahydrofuran. Water (2 mL) was added in 0.5 mL portions, and after addition of 1 mL water, an emulsion due to oiling out was observed. Aging of this emulsion resulted in crystallization. The crystals were isolated on a Buchner funnel.

Example 5: Compound 1 Free Base, Form 4

To a 500 mL round bottom flask was charged 15.0 g (R)-N-(4-chlorophenyl)-2-((1S,4S)-4-(6-fluoroquinolin-4-yl)cyclohexyl)propanamide hydrate and 176 g acetonitrile and stirred until all solids dissolved. The solution was concentrated to dryness under vacuum. An additional 176 g acetonitrile was added and again the solution was concentrated to dryness under vacuum. 134 g ethyl acetate was charged and agitated until it was a homogeneous solution and again concentrated to dryness under vacuum. Once all solvent was removed 50 g ethyl acetate was charged. The solution was heated to 40° C. and agitated via magnetic stirring. Seeds (220 mg) were charged and 144 g heptane was added over 45 min. The slurry was gradually cooled to 20° C. and an additional 27 g heptane was added. The slurry was then subjected to a temperature cycle by heating to 50° C. and cooling gradually to 20° C. The slurry was allowed to agitate overnight. The solids were filtered and dried under vacuum to yield 12.0 g of (R)-N-(4-chlorophenyl)-2-((1S, 4S)-4-(6-fluoroquinolin-4-yl)cyclohexyl)propanamide as a white solid in 84.5% yield.

Example 6: Compound 1 Free Base, Form 4

250 mg of Compound 1 free base was dissolved in 1 mL ethyl acetate at 40° C. 700 uL of heptane was added, followed by about 10 mg of Compound 1 free base Form 4 seeds. This resulted in formation of a slurry. The slurry was aged for 10 min, followed by addition of a further 3 mL of heptane. The slurry was aged for approximately 1 h, then isolated on a Buchner funnel and dried overnight in a vacuum oven at 50° C.

Example 7: Compound 1 Free Base, Form 4

100 mg of Compound 1 free base, Form 2 was dried in a vacuum oven overnight at 50° C. to dehydrate the material. The material was then slurried at 65° C. in 1 mL of heptane overnight. Phase transformation occurred after a few hours, followed by conversion to Compound 1 free base, Form 4.

Example 8: Compound 1 Methanesulfonic Acid (MSA) Salt, Amorphous

To a glass vial 2.6 g of (R)-N-(4-chlorophenyl)-2-((1S, 4S)-4-(6-fluoroquinolin-4-yl)cyclohexyl)propanamide methanesulfonate and 0.1 L of methanol was added. The mixture was stirred at room temperature until the solid dissolved and a clear spray solution resulted. The 2.6% (w/v) spray solution was then spray dried at 65° C. from the methanol solvent using heated nitrogen gas through a two-fluid spraying nozzle (2050 LC/64AC, Spraying Systems Co.) using a custom built small-scale spray dryer. The spray drying parameters applied were: solution spray rate 1.3 mL per minute, inlet $N_2$ gas flow of 32 standard L per minute, 65° C. inlet $N_2$ temperature. Within the spray dryer, solid material was collected on a 4" filter paper. 2.3 g of spray dried white solid was recovered from the filter paper and transferred to a glass vial. The spray dried solid was vacuum dried overnight in a glass vial at room temperature.

Example 8A: Compound 1 Methanesulfonic Acid (MSA) Salt, Amorphous

Rotary evaporation of Compound 1 MSA Salt Form 1 in dichloromethane produced amorphous Compounds 1 MSA salt. The material recrystallized to Compound 1 MSA Salt Form 1 upon heat stressing at 60° C.

Example 9: Compound 1 Methanesulfonic Acid (MSA) Salt, Form 1

50 g of Compound 1 free base was dissolved in 500 mL ethyl acetate at 25° C. in a 1 L reactor with 500 RPM agitation. A solution of 1 molar equivalent of MSA in 250 mL of ethyl acetate was prepared and charged into the reactor via pump over 2 h. The resulting slurry was aged for 30 minutes. The crystals were isolated on a Buchner funnel, dried overnight in 50° C. oven.

Example 10: Compound 1 Methanesulfonic Acid (MSA) Salt, Form 1

To a 10 L glass-lined reactor under a blanket of nitrogen was charged 349 g N,N,N',N'-tetramethylchloroformamidinium hexafluorophosphate (TCFH) and 2 L acetonitrile. 245 g N-methylimidazole was added followed by 0.3 L acetonitrile. 300 g (R)-2-((1S,4S)-4-(6-fluoroquinolin-4-yl) cyclohexyl)propanoic acid was added followed by 0.3 L acetonitrile. The mixture was held for 0.5 h then 139 g 4-chloroaniline charged followed by 0.4 L acetonitrile. The mixture was maintained at 20° C. until the reaction was deemed complete by HPLC analysis. The solution was then heated to 60° C., and 1.2 L water was charged. The solution was then cooled to 40° C., seeds (3 g) were charged, and the resulting slurry was maintained for 1 h. The slurry was then cooled to 20° C. and 2.7 L water was charged. The slurry was filtered and the cake was washed three times with 3 L of 2:1 water/acetonitrile. The cake was dissolved with 5.1 L ethyl acetate and the solution was distilled to a volume of 4.2 L at 41° C. under vacuum. The slurry was cooled to 20° C., 4.14 g seeds were charged, and a solution of 95.7 g methanesulfonic acid in 2.9 L ethyl acetate was added. The slurry was then filtered and washed two times with 1.65 L ethyl acetate and dried under vacuum at 50° C. to yield 445 g of (R)-N-(4-chlorophenyl)-2-((1S,4S)-4-(6-fluoroquinolin-4-yl)cyclohexyl)propanamide methanesulfonate as a white solid in 88% yield.

Example 11: Compound 1 MSA Salt Monohydrate Form 2

Compound 1 MSA Salt monohydrate Form 2 can be prepared by slurrying Compound 1 MSA salt Form 1 at water activities of 60% relative humidity at room temperature of ethanol/water (85/15 v/v). Single crystals of Compound 1 MSA Salt Hydrate Form 2 were grown by evaporating a solution of Compound 1 MSA salt Form 1 in methanol/acetonitrile 8/92 v/v at ambient temperature.

Example 12: Compound 1 MSA Salt Form 1: Solid-State Stability

A 12-month stability study examined the effects of temperature, humidity, and light on Compound 1 MSA Salt Form 1. See table, below. The study consisted of one batch of drug substance packaged in double LDPE bags, placed in a 0.6 L HDPE paid with a lid and gasket. Compound 1 MSA salt Form 1 remained stable up to at least 12 months of storage at the long-term conditions of 5° C. and 25° C./60% relative humidity (RH), 6 months at the accelerated condition of 40° C./75% RH, and 3 months at the stress condition of 50° C. Data from the photostability study indicates that the drug substance does not need to be protected from light. Compound 1 MSA Salt Form 1 can be stored at or below 25° C.

| No. | Stability Study | Storage Conditions | Time | Assay "as is" (%) | Assay "corrected" (%) |
|---|---|---|---|---|---|
| 0 | | | initial | 79.0[1] | 97.0[1] |
| 1 | Long Term | 5° C. | 1 month | 81.9 | 100.5 |
| | | | 3 months | 82.4 | 101.1 |
| | | | 6 months | 81.2 | 99.6 |
| | | | 12 months | 81.7 | 100.5 |
| 2 | | 25° C./60% RH | 1 month | 82.1 | 100.8 |
| | | | 3 months | 81.7 | 100.4 |
| | | | 6 months | 81.2 | 99.7 |
| | | | 12 months | 81.1 | 99.8 |
| 3 | Accelerated | 40° C./75% RH | 2 weeks | 80.7 | 99.1 |
| | | | 1 month | 82.3 | 101.0 |
| | | | 3 months | 81.5 | 100.1 |
| | | | 6 months | 81.8 | 100.4 |
| 4 | Stress | −20° C. | 1 month | 82.4 | 101.1 |
| 5 | | 40° C./75% RH exposed | 2 weeks | 80.9 | 99.3 |
| | | | 1 month | 81.6 | 100.3 |
| | | | 3 months | 81.4 | 99.9 |
| | | | 6 months | 80.3 | 98.6 |
| 6 | | 50° C. | 2 weeks | 80.8 | 99.2 |
| | | | 1 month | 82.0 | 100.7 |
| | | | 3 months | 82.2 | 100.9 |
| 7 | | 25° C./HIL/UVA Exposed | 4 days | 80.8 | 99.2 |
| | | 25° C./HIL/UVA Exposed | 2 weeks | 78.7 | 96.8 |
| | | 25° C./HIL/UVA protected | 4 days | 81.1 | 99.5 |
| | | 25° C./HIL/UVA protected | 2 weeks | 80.4 | 98.7 |

[1]average of 2 results

Essentially no changes were observed is assay "as is" or "corrected" from the initial "as is" value of 79.0% or the assay "corrected" value of 97.0% for study numbers 1, 2, 3, and 5, with some variability. Slight increases were observed in assay "as is" and assay "corrected" from initial values of 79.0% and 97.0%, respectively for study numbers 6 (to 82.0% and 100.7%, respectively) and 4 (to 82.4% and 101.1%, respectively).

Essentially no changes were observed in total impurities from the initial value 0.57% for study numbers 4, 1, 2, and 3. A decrease was observed in total impurities from 0.57% at initial for study numbers 3 (to 0.48%) and 6 (to 0.50%). This was primarily due to a decrease in 4-chloroaniline from 0.09% at initial to <0.05% at both conditions.

No changes were observed in the enantiomeric impurity of Compound 1 from the initial value of <0.05% for study numbers 1 and 2.

Essentially no changes were observed in water content from the initial value of <0.1% w/w for study numbers 1 and 2.

Color and appearance (white or off-white powder or powder with lumps) was maintained during the studies.

No changes in XRD pattern were observed after any of the study numbers.

Essentially no changes were observed when Compound 1 MSA Salt Form 1 was exposed to the minimum ICH Q1B exposure. When subjected to approximately 3.5 times the minimum ICH exposure, a slight increase in total impurities was observed, primarily due to an increase in impurities at levels less than 0.10%. The corrected assay value for the exposed drug substance was observed to be 96.8%. No other changes were observed for any other attributes tested. The data from the photostability study indicate the drug substance does not need to be protected from light.

Compound 1 MSA salt Form 1 was physically stable under stress conditions including milling with organic solvents and water, and stressing at 75% relative humidity at 40° C. for 5 days.

Example 13: Compound 1 MSA Salt Form 1, pH Solubility

The pH solubility of Compound 1 MSA Salt Form 1 was tested using NaOH (1N or 10N aqueous) and HCl (conc. or 1N aqueous) for pH adjustment at 22±3° C. Measurements were taken using an Orion ATI Model 370 pH meter. About 20-30 mg of Compound 1 MSA Salt Form 1 was weighed into each of eleven 10 cc type I glass vials. To each vial was added 5 mL of various aqueous acidic and basic solutions. Each vial was stoppered and vortexed and sonicated to mix well. The pH of each sample was recorded.

Samples were vigorously stirred overnight at ambient room temperature at a speed of 300 rpm. After 24 hours of stirring, the pH of each sample (as a suspension) was recorded. Suspensions were filtered with 0.2 micron Acrodisc syringe filters. The clear filtrates were collected and vortexed to mix well pH of each filtrated was recorded. pH of suspension and filtrate were nearly identical.

A 1.0 mL aliquot of each of the filtrates 25-fold using 50% acetonitrile/50% Milli-Q water, q.w. each flask to 25 mL. Aliquotes were transferred to HPLC autosampler to assay Compound 1 concentration.

Samples were assayed using the following HPLC method:
Column: Waters YMC Pro-Pack C18; Part #AS12S05-1546WT, S-5 µm, 150×4.6 mm ID
Mobile phase Solvent A: Water w/0.05% TFA
Solvent B: Acetonitrile w/0.05% TFA
Flow rate: 1.0 mL/min
Column temperature: Ambient RT
Detector Wavelength: 250 nm
Injection Volume: 10 µL
Working Concentration: Approximately 100 mcg/mL
Sample/Standard Diluent: 50% Acetonitrile/50% Milli-Q Water
Typical Compound 1
Retention Time: 15.5 minutes (RRT 1.0)

| HPLC Program: Gradient | | | |
|---|---|---|---|
| Time/(min) | Flow/(mL/min) | % A | % B |
| 0 | 1.0 | 95 | 5 |
| 24 | 1.0 | 10 | 90 |
| 27 | 1.0 | 95 | 5 |
| 30 | 1.0 | 95 | 5 |

Preparation of external standard: weighed 25.4 mg Compound 1 MSA salt Form 1 into a 25 mL Type I glass vial. Added 20 mL of 100% acetonitrile to the vial. Stoppered, vortexed, and sonicated the vial. All of the solids did not dissolve. Transferred the suspension to a 250 mL glass volumetric flask, and washed out the glass vial with 4×20 mL 50% acetonitrile/50% Milli-Q water, transferring each wash into the volumetric flask. All solids dissolved. Q.S. the volumetric flask to 250 mL final volume using 50% acetonitrile/50% Milli Q water, shake to give standard solution at 101.5 mcg/mL.

The overall profile is typical for a weak base and shows a solubility of 1-2 mcg/mL for the free-base, solubility of ~130 mcg/mL in water (native pH~2.5), pH-max at pH~2 with a solubility of ~560 mcg/mL, and decreasing solubility below pH 2 (73 mcg/mL at pH 1, 24 mcg/mL at pH 0.5). The results are shown in the table, below.

| pH | Compound 1 MSA Salt Form 1 Solubility (mcg/mL) |
|---|---|
| 0.49 | 24 |
| 1.01 | 73 |
| 1.95 | 561 |
| 2.46 | 147 |
| 2.51 (water) | 132 |
| 2.70 | 85 |
| 3.14 | 18 |
| 3.61 | 3 |
| 4.53 | 1 |
| 6.82 | 1 |
| 9.68 | 2 |
| 5.0 (FeSSIF)* | 456 |
| 7.0 (FaSSIF)** | 96 |

*Fed State Simulated Intestinal Fluid
**Fasted State Simulated Intestinal Fluid

Example 14: Microdissolution FaSSiF/FeSSiF

Figure 7:
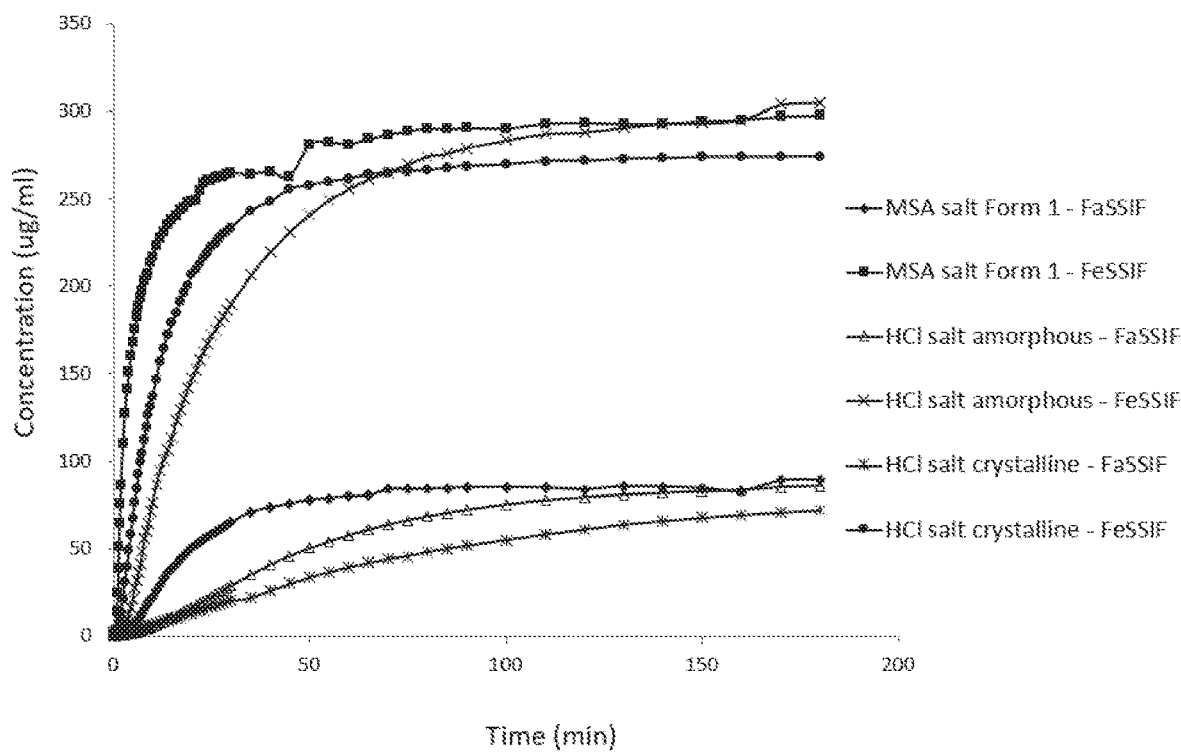
FIG. 7 depicts microdissolution profiles of Compound 1 MSA salt Form 1, Compound 1 HCl (amorphous), crystalline Compound 1 HCl in FaSSI and FeSSIF at simulated 150 mg human dose.

Compound 1 MSA Salt Form 1 displays a faster rate and extent of dissolution as compared to an amorphous form or HCl salts (amorphous and crystalline) in both FeSSiF and FaSSiF. Compound 1 MSA Salt Form 1's rate of dissolution was suggestive of rapid absorption. See FIG. 7.

Figure 8:
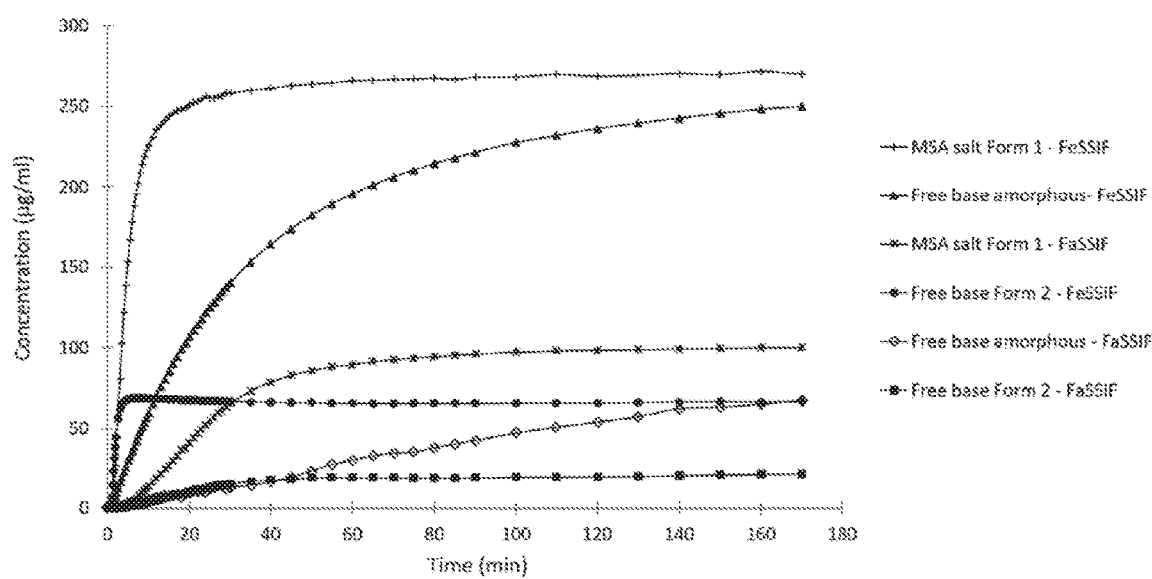
FIG. 8 depicts microdissolution profiles of Compound 1 MSA salt Form 1, Compound 1 free base (amorphous), and Compound 1 free base hydrate Form 2 in FaSSIF and FeSSIF at 0.2 mg/mL, n=3-4.

Compound 1 MSA Salt Form 1 displays a faster rate and extent of dissolution as compared to Compound 1 free base (amorphous). See FIG. 8.

Example 15: Microdissolution FaSSiF/FeSSiF

The dissolution of Compound 1 MSA salt Form 1 and Compound 1 MSA salt monohydrate Form 2 in FaSSIF and FeSSIF was assessed. The target doses were 150 mg in 250 mL (0.60 mg/mL API equivalent) in FaSSIF (pH 6.5) and FeSSIF (pH 5).

Figure 9:
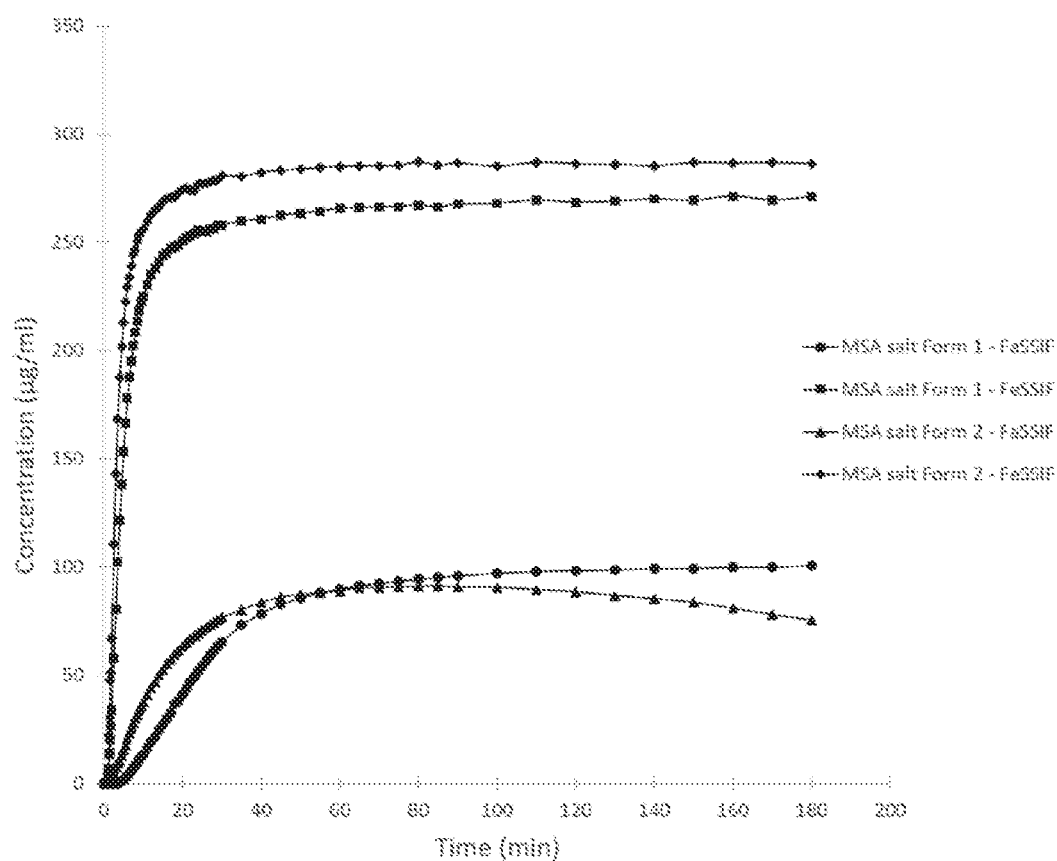
FIG. 9 depicts microdissolution data of Compound 1 MSA salt Form 1 and Compound 1 MSA salt monohydrate Form 2.

The AUC and dissolution rate values appears similar for Compound 1 MSA Salt Form 1 and Compound 1 MSA Salt monohydrate Form 2 in FaSSIF and FeSSIF. There was no statistical difference in AUC values, but a statistically significant difference exists in the dissolution rate with Compound 1 MSA Salt monohydrate Form 2 being slightly faster in FaSSIF. The forms have similar peak solubilities in FaSSIF. Behavior is similar in FeSSIF and is 3-times higher. The food effect ratio for Compound 1 MSA Salt Form 1 was 3.10. The food effect ratio for both forms was constant. Compound 1 MSA Salt hydrate Form 2 food effect ratio was 3.49. See table, below, and FIG. 9. Compound 1 MSA salt hydrate Form 2 appears to have a similar dissolution profile as Compound 1 MSA salt Form 1.

Example 16: Microdissolution FaSSiF/FeSSiF

This study assessed the dissolution difference of Compound 1 free base (amorphous), Compound 1 free base Form 2, and Compound 1 MSA Salt Form 1 in FaSSIF and FeSSIF.

The Compound 1 MSA salt Form 1 peak solubility is 4-5 times higher in both FaSSIF and FeSSIF than the free base Form 2. This is statistically significant (p<0.05). The rate of dissolution for the Compound 1 MSA salt Form 1 in FeSSIF is 38 vs. 23 ug/mL/min. In FeSSIF, the rate and extent of dissolution increases for all APIs. The FE ratio for the MSA salt for is about 3.5, amorphous free base is 5, freebase Form 2 is ~3.5.

Example 17: Jet-Milling

Particle size reduction can be achieved by jet milling using a 0202 Jet o Mizer loop Mill. Particle collisions are enabled by nitrogen gas supplied at high pressure to the milling chamber via two grinding nozzles. The feed rate of the drug substance into the mill is controlled by a feeder that supplies drug substance into the feed hopper of the mill at a visually consistent feed rate. High pressure nitrogen gas is supplied through the venturi nozzle to inject drug substance from the mill feed hopper into the milling chamber, and this is referred to as the venture pressure. The grinding and venturi pressures are adjusted to the desired level before the start of milling, and both are kept at the same level unless product blow back from the feed hopper is observed. The venturi pressure is typically adjusted to 10 PSI above the grinding pressure. The micronized drug substance exits via the mill chamber outlet to be collected in the product collection unit consisting of a combined cyclone and porous fabric filter media assembly. Milling parameters may be adjusted based on sample analysis. Particle sizes that range between 12.7 μm and 24.0 μm (D90 by laser-light scattering) are achieved from the milling operation. Milling parameters and physical properties are shown in the table, below.

| Material Property | Range from 0202 Jet Mill |
|---|---|
| Color and appearance | White powder |
| Feed rate range (kg/hr) | 1.18-2.22 |
| Mill pressure range (psig) | 20-65 |
| Mill pressure range (barg) | 20-65 |
| D50 (μm) | 6.2-9.8 |
| D90 (μm) | 12.7-24.0 |
| Surface area (m$^2$/g) | 2.08-3.63 |
| Bulk density (g/mL) (for sample with D90 of 22.3 μm) | 0.193 |

| Compound 1 MSA Salt | AUC (ug · min/mL) | | | Dissolution Rate (ug/mL/min) | | Peak Solubility (ug/mL) |
|---|---|---|---|---|---|---|
| | Mean | SD | % CV | Mean | SD | Mean |
| Form 1 FaSSIF | 14988.073 | 1160.442 | 7.742 | 2.460 | 0.466 | 100.877 |
| Form 1 FeSSIF | 46410.396 | 2091.297 | 4.506 | 38.850 | 9.664 | 271.564 |
| Form 2 FaSSIF | 14315.281 | 657.354 | 4.592 | 4.449 | 0.654 | 91.325 |
| Form 2 FeSSIF | 50014.687 | 5376.308 | 10.749 | 47.996 | 3.879 | 287.395 | p-value (Form 2 v. Form 2, FaSSIF) AUC = 0.352, rate = 0.003
p-value (Form 2 v. Form 2, FeSSIF) AUC = 0.329, rate = 0.139

Example 18: Stability—Compound 1 Free Base Form 4

Solid state stability of Compound 1 free base Form 4 was conducted. The results of those experiments are in the table, below. No changes were observed for at least 2 weeks.

Compound 1 free base form 4 is chemically stable for at least 4 weeks.

| Stress Conditions | 2-week Area % | 4-week Area % |
| --- | --- | --- |
| RT/RL* | 99.75% | 99.70% |
| 25° C./60% relative humidity | 99.78% | 99.77% |
| 40° C./75% relative humidity (open) | 99.79% | 98.46% |
| 40° C./75% relative humidity (closed) | 99.78% | 99.71 |
| 50° C. | 99.68% | 99.74% |
| High intensity light (HIL) | 99.77% | 99.58% |

*room temperature/room light

Example 19: Stability—Compound 1 Free Base Hydrate Form 2

Solid state stability of Compound 1 Free Base monohydrate Form 2 was conducted. The results of those experiments are in the table, below. No changes in PXRD were observed at 4 weeks or 8 weeks in all samples. No changes in DSC/TGA were observed at 4 weeks in all samples. There was no evidence of form change, dehydration, or amorphous formation after 8 weeks. There was no change in TGA at 8 weeks in all samples.

Compound 1 free base hydrate Form 2 is chemically stable for at least 13.5 weeks at elevated temperature and humidity conditions tested.

| Stress Conditions | 4-week Area % | 8-week Area % | 13.5 week Area % |
| --- | --- | --- | --- |
| RT/RL* | 99.90% | 99.90% | 99.78% |
| 25° C./60% relative humidity | 99.90% | 99.90% | 99.73% |
| 40° C./75% relative humidity (open) | 99.90% | 99.90% | 99.63% |
| 40° C./75% relative humidity (closed) | 99.90% | 99.90% | 99.62% |
| 50° C. | 99.90% | 99.04% | 99.79% |
| High intensity light (HIL) | 99.1% | ND | ND |

*room temperature, room light

Example 20

Amorphous Compound 1 MSA material converted to Compound 1 MSA Salt Form 1 upon heat stressing at 60° C. after 9 days. Compound 1 MSA salt monohydrate Form 2 converts to Compound 1 MSA Salt Form 1 and Compound 1 MSA Salt monohydrate form 2 after stressing at 75% relative humidity at 40 C for 6 days. Partial conversion to Compound 1 MSA salt monohydrate Form 2 at 75% relative humidity suggests that the X-ray amorphous material may have a faster conversion rate to Compound 1 MSA salt hydrate Form 2 than Compound 1 MSA salt Form 1.

Example 21: Stability—Compound 1 Free Base

Heating experiments were performed to study any form changes that might occur in Compound 1 Free Base Monohydrate Form 2, Compound 1 Free Base Form 4, and Compound 1 Free Base Amorphous.

Compound 1 Free Base Amorphous was heated between 67° C. and 150° C. No crystallization was observed. A melt/quench experiment starting with Compound 1 Free Base Form 4 resulted in a glass with a few fine, birefringent acicular particles, although the resulting XRPD pattern did not exhibit evidence of crystalline material.

Compound 1 Free Base Monohydrate Form 2 was heated at −100° C. for ~2 hours, resulting in an observable change in birefringence but no form change by XRPD. Heating to ~125° C. caused the sample to liquefy. Cooling of the liquid sample on dry ice produced a non-birefringent glass consistent with X-ray amorphous material. Additional heating experiments for Compound 1 Free Base Monohydrate Form 2, in which the material was heated at ~79 to 80° C. for 1 day or at ~75° C. under nitrogen gas flow for ~20 hours, both caused partial conversion to other crystalline forms. Compound 1 Free Base Monohydrate Form 2 is likely the thermodynamically stable form at high relative humidity and RT.

A number of experiments were set up to explore dehydration of hydrated forms at ~0% RH. Compound 1 Free Base Monohydrate Form 2 converted to an unstable form after an overnight hold at 0% RH.

What is claimed:

1. Crystalline (R)-N-(4-chlorophenyl)-2-((1S,4S)-4-(6-fluoroquinolin-4-yl) cyclohexyl)propanamide Form 4, characterized by a powder X-ray diffraction pattern comprising at least one peak selected from 7.6, 12.0, 13.5, 14.4, 17.6, 20.1, 20.7, and 22.0 degrees 2θ±0.2 degrees 2θ.

2. The crystalline (R)-N-(4-chlorophenyl)-2-((1S,4S)-4-(6-fluoroquinolin-4-yl)cyclohexyl)propanamide Form 4 of claim 1, characterized by a powder X-ray diffraction pattern comprising two peaks selected from 7.6, 12.0, 13.5, 14.4, 17.6, 20.1, 20.7, and 22.0 degrees 2θ±0.2 degrees 2θ.

3. The crystalline (R)-N-(4-chlorophenyl)-2-((1S,4S)-4-(6-fluoroquinolin-4-yl)cyclohexyl)propanamide Form 4 of claim 1, characterized by a powder X-ray diffraction pattern comprising three peaks selected from 7.6, 12.0, 13.5, 14.4, 17.6, 20.1, 20.7, and 22.0 degrees 2θ±0.2 degrees 2θ.

4. The crystalline (R)-N-(4-chlorophenyl)-2-((1S,4S)-4-(6-fluoroquinolin-4-yl)cyclohexyl)propanamide Form 4 of claim 1, characterized by a powder X-ray diffraction pattern comprising four peaks selected from 7.6, 12.0, 13.5, 14.4, 17.6, 20.1, 20.7, and 22.0 degrees 2θ±0.2 degrees 2θ.

* * * * *